US012723038B2

(12) United States Patent
Carter et al.

(10) Patent No.: US 12,723,038 B2
(45) Date of Patent: Sep. 1, 2026

(54) $\alpha_{1A}$-ADRENERGIC RECEPTOR AGONISTS AND METHODS OF USE

(71) Applicant: CuraSen Therapeutics, Inc., San Carlos, CA (US)

(72) Inventors: David Scott Carter, San Carlos, CA (US); Anthony P. Ford, San Carlos, CA (US)

(73) Assignee: CuraSen Therapeutics, Inc., San Carlos, CA (US)

(*) Notice: Subject to any disclaimer, the term of this patent is extended or adjusted under 35 U.S.C. 154(b) by 479 days.

(21) Appl. No.: 18/022,949

(22) PCT Filed: Aug. 26, 2021

(86) PCT No.: PCT/US2021/047779

§ 371 (c)(1),
(2) Date: Feb. 23, 2023

(87) PCT Pub. No.: WO2022/047052

PCT Pub. Date: Mar. 3, 2022

(65) Prior Publication Data

US 2023/0312524 A1 Oct. 5, 2023

Related U.S. Application Data

(60) Provisional application No. 63/071,297, filed on Aug. 27, 2020.

(51) Int. Cl.

| | |
|---|---|
| ***C07D 233/06*** | (2006.01) |
| ***A61K 31/4174*** | (2006.01) |
| ***A61K 31/4178*** | (2006.01) |
| ***A61K 31/422*** | (2006.01) |
| ***A61K 31/427*** | (2006.01) |
| ***A61K 31/4439*** | (2006.01) |
| ***A61K 31/497*** | (2006.01) |
| ***A61K 31/501*** | (2006.01) |
| ***A61K 31/506*** | (2006.01) |
| ***A61K 31/5355*** | (2006.01) |
| ***A61P 25/28*** | (2006.01) |
| ***C07D 233/20*** | (2006.01) |
| ***C07D 233/22*** | (2006.01) |
| ***C07D 233/24*** | (2006.01) |
| ***C07D 233/26*** | (2006.01) |
| ***C07D 401/10*** | (2006.01) |
| ***C07D 403/06*** | (2006.01) |
| ***C07D 403/10*** | (2006.01) |
| ***C07D 403/14*** | (2006.01) |
| ***C07D 405/06*** | (2006.01) |
| ***C07D 405/10*** | (2006.01) |
| ***C07D 409/10*** | (2006.01) |
| ***C07D 413/10*** | (2006.01) |
| ***C07D 417/10*** | (2006.01) |

(52) U.S. Cl.
CPC ......... *C07D 403/10* (2013.01); *C07D 233/22* (2013.01); *C07D 405/06* (2013.01)

(58) Field of Classification Search
CPC .. C07D 233/06; C07D 233/20; C07D 233/22; C07D 233/24; C07D 233/26; C07D 401/10; C07D 403/06; C07D 403/10; C07D 403/14; C07D 405/06; C07D 405/10; C07D 409/10; C07D 413/10; C07D 417/10; A61K 31/4178; A61K 31/422; A61K 31/506; A61K 31/427; A61K 31/4174; A61K 31/4439; A61K 31/497; A61K 31/5355; A61K 31/501; A61P 25/28
See application file for complete search history.

(56) References Cited

U.S. PATENT DOCUMENTS

| | | | | |
|---|---|---|---|---|
| 2,161,938 | A | 6/1939 | Sonn | |
| 2,919,274 | A | 12/1959 | Faust et al. | |
| 3,423,423 | A | 1/1969 | White | |
| 4,665,094 | A | 5/1987 | Baldwin et al. | |
| 5,952,362 | A | 9/1999 | Cournoyer et al. | |
| 6,756,395 | B2 * | 6/2004 | Dillon | A61P 25/00 514/401 |
| 6,852,726 | B2 | 2/2005 | Greenhouse et al. | |
| 7,407,980 | B2 * | 8/2008 | Dillon | A61P 25/00 514/401 |
| 7,528,175 | B2 | 5/2009 | Bond | |

(Continued)

FOREIGN PATENT DOCUMENTS

| | | | |
|---|---|---|---|
| CA | 2246027 | A1 | 2/2000 |
| CN | 1515562 | A | 7/2006 |

(Continued)

OTHER PUBLICATIONS

CAS printout of the search with the species found with adrenegic receptor activity (Year: 2025).*

(Continued)

*Primary Examiner* — Brenda L Coleman
(74) *Attorney, Agent, or Firm* — DLA Piper LLP (US)

(57) ABSTRACT

The present disclosure relates generally to chemical compounds and, in some embodiments, to α1A-adrenergic receptor agonists and uses of such agonists in the treatment of diseases associated with an adrenergic receptor. Disclosed herein is a compound according to Formula (I) or an optically pure stereoisomer, pharmaceutically acceptable salt, solvate, or prodrug thereof.

12 Claims, No Drawings

(56) References Cited

U.S. PATENT DOCUMENTS

| | | | | |
|---|---|---|---|---|
| 7,799,816 | B2 * | 9/2010 | O'Yang | C07D 233/24 514/401 |
| 8,796,293 | B2 | 8/2014 | Davies et al. | |
| 9,539,221 | B2 | 1/2017 | Bond | |
| 11,590,107 | B2 * | 2/2023 | Ford | A61K 31/4164 |
| 2003/0229130 | A1 | 12/2003 | Dillon et al. | |
| 2007/0197621 | A1 | 8/2007 | Galley et al. | |
| 2009/0197933 | A1 | 8/2009 | O-Yang et al. | |
| 2015/0011630 | A1 | 1/2015 | Goldstein et al. | |
| 2018/0230105 | A1 | 8/2018 | More et al. | |
| 2019/0117623 | A1 | 4/2019 | Simpson, Jr. | |
| 2022/0401415 | A1 * | 12/2022 | Ford | A61K 31/4164 |

FOREIGN PATENT DOCUMENTS

| | | |
|---|---|---|
| DE | 1302902 | 12/1971 |
| JP | S51-106739 | 9/1976 |
| JP | S62-145067 | 6/1987 |
| JP | 2000-511903 A | 9/2000 |
| JP | 2011-511024 | 4/2011 |
| JP | 2013/199432 A | 10/2013 |
| JP | 2015-193573 A | 11/2015 |
| PL | 217013 B1 | 6/2014 |
| WO | WO 2004/009090 A1 | 1/2004 |
| WO | WO 2009/098136 A1 | 8/2009 |
| WO | WO 2009/128479 A1 | 10/2009 |
| WO | WO 2016/105448 A1 | 6/2016 |

OTHER PUBLICATIONS

Machine Translation of JP 2013/199432 Oct. 3, 2013.*

EP Extended Search Report in European Application No. 20878218.5, dated Oct. 17, 2023, 8 pages.

Boblewski et al., "Circulatory effect of TCS-80, a new imidazoline compound, in rats", Pharmacological Reports, Mar. 2016, 68: 715-719.

PCT International Search Report and Written Opinion in International Application No. PCT/US2023/15914, Aug. 16, 2023, 12 pages.

PubChem CID 22574001, "1-(4,5-Dihydrro-1H-imidazol-2-ylmethyl)-1H-indole", PubChem, Dec. 5, 2007, 10 pages.

PubChem CID 57391904, "1-(4,5-dihydro-1H-imidazol-2-ylmethyl)indazol", PubChem, Jul. 25, 2012, 8 pages.

Carissimi et al., "Unknown", Farmaco, Database Accession No. 532511, Jan. 1962, 17:81-89, 1 page.

EP Partial Supplementary Search Report in European Application No. 21862751.1, dated Sep. 6, 2024, 28 pages.

Galley et al., "Optimization of imidazole compounds as selective TAAR1 agonists: Discovery of RO5073012", Jun. 2012, 22(16): 5244-5248.

Nardi et al., "Research on durene derivatives. Note I. Hypertensive activity of 2-(2,3,5,6-tetramethylbenzyl) imidazoline and related compounds", Farmaco, Jan. 1979, 34(9): 789-801, 1 page.

Prisinzano et al., "2-(anilino) imidazoline derivatives as h5-HT1D serotonin receptor ligands", Bioorganic & Medicinal Chemistry Letters, Sep. 2004, 14(18): 4697-4699.

Suzuki et al., "Discovery of potent [alpha] 1L-adrenoceptor agonists: Design and synthesis of bicyclic derivatives", Bioorganic & Medicinal Chemistry Letters, May 2015, 25(16): 3368-3372.

Verrier et al., "GPCRs regulate the assembly of a multienzyme complex for purine biosynthesis", Nature Chemical Biology, Jan. 2011, 7: 909-915.

Venkataraman, et al., "Structure-activity studies of new imidazolines on adrenoceptors of rat aorta and human platelets," Naunyn-Schmiedeberg's Archives of Pharmacology, 1991, 344(4), pp. 454-463.

Miller, et al., "Synthesis and alpha2-Adrenoceptor Effects of Substituted Catecholimidizaline and Catecholimidazole Analogues in Human Platelets," Journal of Medicinal Chemistry, 1990, 33(4), pp. 1138-1144.

Law, et al., "Benzylimidazolines as h5-HT1B/1D Serotonin Receptor Ligands: a Structure-Affinity Investigation," Journal of Medicinal Chemistry, 1998, 41(13), pp. 2243-2251.

RN 1368426-44-1, etc. (total 29 species), Database Registry [Online], Retrieved from STN, 2025, 29 pages.

Notice of Reasons for Rejection for JP2023-513294 mailed Jul. 8, 2025, 13 pages.

Montgomery, et al., "An Alpha-1A Adrenergic Receptor Agonist Prevents Acute Doxorubicin Cardiomyopathy in Male Mice," PLOS ONE, Jan. 12, 2017, 22 pages.

Beak, et al., "An Oral Selective Alpha-1A Adrenergic Receptor Agonist Prevents Doxorubicin Cardiotoxicity," JACC: Basic to Translational Science, vol. 2, No. 1, Feb. 2017, pp. 29-53.

Cowley, et al., "Reversal of right ventricular failure by chronic Alpha-1A-subtype adrenergic agonist therapy," Am J Physiol Heart Circ Physiol 316, Nov. 9, 2018, pp. H224-H232.

Janssen, et al., "Human Myocardium Has a Robust Alpha-1A-Subtype Adrenergic Receptor Inotropic Response," J Cardiovasc Pharmacol, Sep. 2018, 72(3), 15 pages.

Jensen, et al., "Alpha-1-adrenergic receptors: Targets for agonist drugs to treat heart failure," Journal of Molecular and Cellular Cardiology 51, (2011), pp. 518-528.

Saczewski, Jaroslaw, et al., "Transfer of SAR information from hypotensive indazole to indole derivatives acting at $\alpha$-adrenergic receptors: In vitro and in vivo studies," European Journal of Medicinal Chemistry, 115, (2016) pp. 406-415.

Wasilewska, Aleksandra, et al., "Fluorinated analogues of marsanidine, a highly $\alpha_2$-AR/imidazoline $I_1$ binding site-selective hypotensive agent. Synthesis and biological activities," European Journal of Medicinal Chemistry, 87, (2014), pp. 386-397.

Saczewski, Jaroslaw, et al., "Synthesis and biological activities of 2-[(heteroaryl)methyl]imidazolines," Bioorganic and Medicinal Chemistry, 20, (2012), pp. 108-116.

Surman, Matthew D., et al., "5-(Pyridinon-1-yl)indazoles and 5-(furopyridinon-5-yl)indazoles," Bioorganic and Medicinal Chemistry Letters, 20, (2010), pp. 7015-7019.

Partial Supplementary European Search Report for EP Application No. 23775602.8 mailed Feb. 23, 2026, 19 pages.

* cited by examiner

$\alpha_{1A}$-ADRENERGIC RECEPTOR AGONISTS AND METHODS OF USE

CROSS REFERENCE TO RELATED APPLICATIONS

This application is a 35 USC § 371 National Stage application of International Application No. PCT/US2021/047779 filed Aug. 26, 2021; which claims the benefit under 35 USC § 119(e) to U.S. Application Ser. No. 63/071,297 filed Aug. 27, 2020. The disclosure of each of the prior applications is considered part of and is incorporated by reference in the disclosure of this application.

BACKGROUND OF THE INVENTION

Field of the Invention

The present disclosure relates generally to chemical compounds and, in some embodiments, to $\alpha_{1A}$-adrenergic receptor agonists and uses in the treatment of diseases associated with an adrenergic receptor.

PCT Patent Application Publication No. WO2008112773 states "the application is directed to the use of droxidopa, alone or in combination with one or more additional components, for the treatment of conditions, such as neuronally mediated postural hypotension."

U.S. Pat. No. 5,952,362 discloses "various 2-imidazoline, 2-oxazoline, 2-thiazoline, and 4-imidazole derivatives of methylphenyl, methoxyphenyl, and aminophenyl alkylsulfonamides and ureas" and "includes the use of the above compounds, and compositions containing them, as alpha$_{1A/1L}$ agonists in the treatment of various disease states such as urinary incontinence, nasal congestion, priapism, depression, anxiety, dementia, senility, Alzheimer's, deficiencies in attentiveness and cognition, and eating disorders such as obesity, bulimia, and anorexia." The '362 patent discloses the compound N-[6-chloro-3-(4,5-dihydro-1H-imidazol-2-ylmethoxy)-2-methylphenyl] methanesulfonamide hydrochloride.

SUMMARY OF THE INVENTION

The present disclosure is based at least in part on the identification of compounds that modulate adrenergic receptor and methods of using the same to treat diseases associated with an adrenergic receptor. Disclosed herein is a compound according to Formula (I) or an optically pure stereoisomer, pharmaceutically acceptable salt, solvate, or prodrug thereof.

Formula (I)

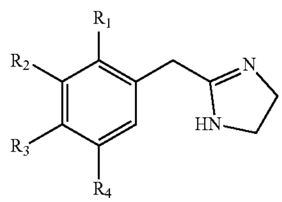

In some embodiments, $R_1$, $R_2$, $R_3$, and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments, $R_1$ and $R_2$ together with the C atoms to which they are attached optionally form an unsubstituted or substituted 5- to 8-membered heterocyclic ring having at least one nitrogen or oxygen atom, $R_2$ and $R_3$ together with the C atoms to which they are attached optionally form an unsubstituted or substituted 5- to 8-membered heterocyclic ring having at least one nitrogen or oxygen atom, or $R_3$ and $R_4$ together with the C atoms to which they are attached optionally form an unsubstituted or substituted 5- to 8-membered heterocyclic ring having at least one nitrogen or oxygen atom.

In some embodiments, at least two of $R_1$, $R_2$, $R_3$, and $R_4$ are not hydrogen if $R_1$ and $R_2$ together with the C atoms to which they are attached does not form an unsubstituted or substituted 5- to 8-membered heterocyclic ring having at least one nitrogen or oxygen atom, $R_2$ and $R_3$ together with the C atoms to which they are attached does not form an unsubstituted or substituted 5- to 8-membered heterocyclic ring having at least one nitrogen or oxygen atom, and $R_3$ and $R_4$ together with the C atoms to which they are attached does not form an unsubstituted or substituted 5- to 8-membered heterocyclic ring having at least one nitrogen or oxygen atom.

Also disclosed herein are compounds according to the structure of Formula Formula (I')

Formula (I')

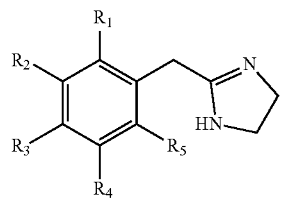

or pharmaceutically acceptable salt thereof, wherein:

$R_1$, $R_2$, $R_3$, $R_4$, and $R_5$ are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted cycloalkoxy, unsubstituted or substituted heterocycloalkyl, unsubstituted or substituted heterocycloalkoxy, unsubstituted or substituted aryl, and unsubstituted or substituted heteroaryl, or:

$R_1$ and $R_2$ together with the C atoms to which they are attached optionally form an unsubstituted or substituted 5- to 9-membered heterocyclic ring having at least one nitrogen or oxygen atom, $R_2$ and $R_3$ together with the C atoms to which they are attached optionally form an unsubstituted or substituted 5- to 9-membered heterocyclic ring having at least one nitrogen or oxygen atom, or $R_3$ and $R_4$ together with the C atoms to which they are attached optionally form an unsubstituted or substituted 5- to 9-membered heterocyclic ring having at least one nitrogen or oxygen atom, wherein at least two of $R_1$, $R_2$, $R_3$, $R_4$, and $R_5$ are not hydrogen.

Also disclosed herein are compounds according to the structure of Formula (I-a) or an optically pure stereoisomer, pharmaceutically acceptable salt, solvate, or prodrug thereof, wherein $R_1$, $R_2$, $R_3$, and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Formula (I-a)

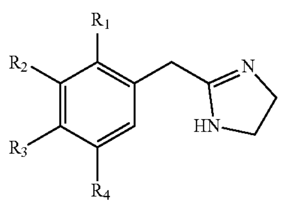

In some embodiments, at least two of $R_1$, $R_2$, $R_3$, and $R_4$ are not hydrogen.

Also disclosed herein is a compound according to Formula (I-b) or an optically pure stereoisomer, pharmaceutically acceptable salt, solvate, or prodrug thereof, wherein $R_1$ and $R_2$ together with the C atoms to which they are attached form an unsubstituted or substituted 5- to 8-membered heterocyclic ring having at least one nitrogen or oxygen atom.

Formula (I-b)

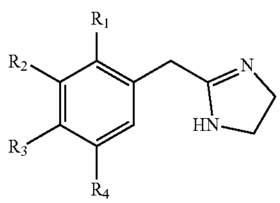

In some embodiments, $R_3$ and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein is a compound according to Formula (I-c) or an optically pure stereoisomer, pharmaceutically acceptable salt, solvate, or prodrug thereof, wherein $R_2$ and $R_3$ together with the C atoms to which they are attached form an unsubstituted or substituted 5- to 8-membered heterocyclic ring having at least one nitrogen or oxygen atom.

Formula (I-c)

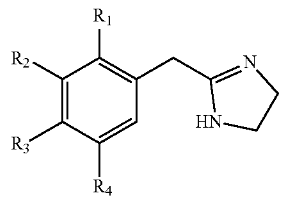

In some embodiments, $R_1$ and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein is a compound according to Formula (I-d) or an optically pure stereoisomer, pharmaceutically acceptable salt, solvate, or prodrug thereof, wherein $R_3$ and $R_4$ together with the C atoms to which they are attached form an unsubstituted or substituted 5- to 8-membered heterocyclic ring having at least one nitrogen or oxygen atom.

Formula (I-d)

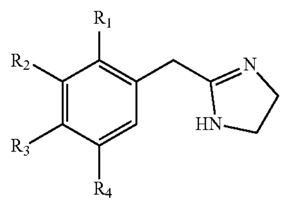

In some embodiments, $R_1$ and $R_2$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein are compounds according to the structure of Formula (II) or an optically pure stereoisomer, pharmaceutically acceptable salt, solvate, or prodrug thereof.

Formula (II)

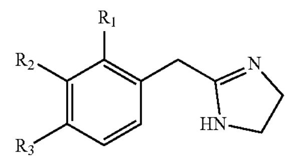

In some embodiments, $R_1$, $R_2$, and $R_3$, are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments, at least two of $R_1$, $R_2$, $R_3$, and $R_4$ are not hydrogen.

Also disclosed herein are compounds according to the structure of Formula (III) or an optically pure stereoisomer, pharmaceutically acceptable salt, solvate, or prodrug thereof.

Formula (III)

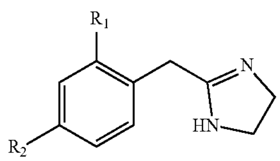

In some embodiments, $R_1$ and $R_2$ are independently selected from the group consisting of deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein are compounds according to the structure of Formula (IV) or an optically pure stereoisomer, pharmaceutically acceptable salt, solvate, or prodrug thereof.

Formula (IV)

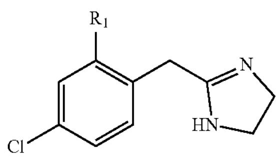

In some embodiments, $R_1$ is independently selected from the group consisting of deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments a compound as disclosed herein is an agonist, partial agonist or antagonist of an adrenergic receptor; in some embodiments the compound is an $\alpha_{1A}$-adrenergic receptor agonist; in some embodiments the compound is an $\alpha_{1A}$-adrenergic receptor partial agonist; in some embodiments the compound is an $\alpha_{1A}$-adrenergic receptor antagonist.

Also disclosed herein is a pharmaceutical composition including a compound as disclosed herein, i.e., a compound with a structure of Formula (I), Formula (I'), Formula (I-a), Formula (I-a'), Formula (I-b), Formula (I-b'), Formula (I-c), Formula (I-c'), Formula (I-d), Formula (I-d'), Formula (I-e'), Formula (I-f'), Formula (I-g'), Formula (I-h'), Formula (I-i'), Formula (I-j'), Formula (II), Formula (II'), Formula (III), Formula (III'), Formula (IV), or Formula (IV') and a pharmaceutically acceptable excipient.

Further disclosed is a method of treating a subject with a disease, the method including administering to the subject a therapeutically effective amount of a compound as disclosed herein, i.e., a compound with a structure of Formula (I), Formula (I'), Formula (I-a), Formula (I-a'), Formula (I-b), Formula (I-b'), Formula (I-c), Formula (I-c'), Formula (I-d), Formula (I-d'), Formula (I-e'), Formula (I-f'), Formula (I-g'), Formula (I-h'), Formula (I-i'), Formula (I-j'), Formula (II), Formula (II'), Formula (III), Formula (III'), Formula (IV), or Formula (IV'). In some embodiments, the disease is a disease associated with an adrenergic receptor. In some embodiments, the disease is a neurodegenerative disease. In some embodiments, the subject is a human.

In some embodiments, the disease is selected from myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, and neuronal ceroid lipofuscinosis. In some embodiments, the compound is administered to the subject through oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route.

In some embodiments, the disease is a neurodegenerative disease that is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CID etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS). In some embodiments the disease is a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder). In some embodiments the subject does not have Alzheimer's disease (AD). In some embodiments the subject does not have Down Syndrome.

Also disclosed is a method of treating a subject with a nOH, the method including administering to the subject a therapeutically effective amount of a compound as disclosed herein, i.e., a compound with a structure of Formula (I), Formula (I'), Formula (I-a), Formula (I-a'), Formula (I-b), Formula (I-b'), Formula (I-c), Formula (I-c'), Formula (I-d), Formula (I-d'), Formula (I-e'), Formula (I-f'), Formula (I-g'), Formula (I-h'), Formula (I-i'), Formula (I-j'), Formula (II), Formula (II'), Formula (III), Formula (III'), Formula (IV), or Formula (IV').

The term "partial agonist" as used herein means a ligand that acts as an agonist to a receptor but does not reach the maximal response capability of the system even at full receptor occupancy; i.e., a partial agonist produces submaximal activation even when occupying the total receptor population, therefore cannot produce the maximal response, irrespective of the concentration applied. In some embodiments, a partial agonist exhibits a maximum efficacy that is less than 1%; or 5%; or 10%; or 15%; or 20%; or 25%; or 30%; or 35%; or 40%; or 45%; or 50%; or 55%; or 60%; or 65%; or 70%; or 75%; or 80%; or 85% of the efficacy of a corresponding full agonist of the same receptor (examples of a full agonist of the $\alpha_{1A}$-adrenergic receptor include noradrenaline and amidephrine).

The term "$\alpha_{1A}$-adrenergic receptor partial agonist" as used herein means a ligand that is a partial agonist of the $\alpha_{1A}$-adrenergic receptor. In this application, the terms "$\alpha_{1A}$-adrenergic receptor partial agonist", "$\alpha_{1A}$-ADR partial agonist", "$\alpha_{1A}$-AR agonist" and "$\alpha_{1A}$ partial agonist" may be used interchangeably. In some embodiments an $\alpha_{1A}$-adrenergic partial agonist exhibits a maximum efficacy (or intrinsic activity, "IA") that is less than 10%; or less than 15%; or less than 20%; or less than 25%; or less than 30%; or less than 35%; or less than 40%; or less than 45%; or less than 50%; or less than 55%; or less than 60%; or less than 65%; or less than 70%; or less than 75%; or less than 80%; or less than 85% or between 15 and 75%; or between 20 and 65%; or between 20 and 60%; or between 20 and 55%; or between 20 and 50%; or between 20 and 45%; or between 25 and 60%; or between 25 and 55%; or between 25 and 35%; or between 30 and 40%; or between 40 and 50%; or between 45 and 55%; of the intrinsic activity of a corresponding full agonist of the $\alpha_{1A}$-adrenergic receptor (examples of a full agonist of the $\alpha_{1A}$-adrenergic receptor include noradrenaline and amidephrine). In some embodiments an $\alpha_{1A}$-adrenergic partial agonist exhibits a maximum efficacy (or intrinsic activity, "IA") that is less than 30%; or less than 35%; or less than 40%; or less than 45%; or less than 50%; or less than 55%; or less than 60%; or less than 65%; or less than 70%; or less than 75%; or less than 80%; or less than 85% —but that is greater than 5%; or 10%; or 15% or 20%. Blue et al., *BJU International*, (2004) 93:162-170 (hereby incorporated by reference in its entirety) provides compositions and methods that can be used to determine partial agonism, and partial agonism of the $\alpha_{1A}$-adrenergic receptor in particular, and demonstrates exemplary $\alpha_{1A}$-adrenergic partial agonists. In certain embodiments, an $\alpha_{1A}$-ADR partial agonist has less than 35%; or less than 40%; or less than 45%; or less than 50%; or less than 55%; or less than 60%; or less than 65%; or less than 70%; or less than 75%; or less than 80%; or less than 85%; or between 15 and 75%; or between 20 and 65%; or between 25 and 60%; or between 25 and 55%; or between 25 and 35%; or between 30 and 40%; or between 40 and 50%; or between 45 and 55% of the activity of a full agonist using the InsPs accumulation assay described in Blue et al. (see, for example, Blue et. al., Table 1 showing an intrinsic activity of 0.31 for RO 115-1240 (dabuzalgron) free base and 0.27 for RO 115-1240 (dabuzalgron) HCl salt as compared to noradrenaline in the InsPs accumulation assay). In some embodiments, an $\alpha_{1A}$-ADR partial agonist has less than 35%; or less than 40%; or less than 45%; or less than 50%; or less than 55%; or less than 60%; or less than 65%; or less than 70%; or less than 75%; or less than 80%; or less than 85% or between 15 and 75%; or between 20 and 65%; or between 25 and 60%; or between 25 and 55%; or between 25 and 35%; or between 30 and 40%; or between 40 and 50%; or between 45 and 55% of the activity of a full agonist using the FLIPR assay described in Blue et al. (see, for example, Blue et al., Table 1 showing an intrinsic activity of 0.51 for RO 115-1240 (dabuzalgron) HCl salt as compared to noradrenaline in the FLIPR assay). In many embodiments, an $\alpha_{1A}$-ADR partial agonist may have a similar affinity for the $\alpha_{1A}$-adrenergic receptor as compared to a full agonist. The term $\alpha_{1A}$-ADR partial agonist as used herein contemplates in some embodiments any pharmaceutically acceptable salt, or prodrug thereof.

In some embodiments, an $\alpha_{1A}$-ADR partial agonist is a selective $\alpha_{1A}$-adrenergic partial agonist. As used herein a "selective $\alpha_{1A}$-ADR partial agonist" exhibits partial agonism for $\alpha_{1A}$-adrenergic receptors but does not exhibit appreciable agonism for other receptors, such as other $\alpha_1$-adrenergic receptor subtypes (e.g., $\alpha_{1B}$-ADR or $\alpha_{1D}$-ADR). Blue et al., *BJU International*, (2004) 93:162-170 (hereby incorporated by reference in its entirety) provides compositions and methods that can be used to determine selective agonism (and selective partial agonism), and selective agonism (and selective partial agonism) of the $\alpha_{1A}$-ADR receptor in particular, and demonstrates exemplary selectivities as $\alpha_{1A}$-ADR partial agonists. In some embodiments, a selective $\alpha_{1A}$-ADR agonist or a selective $\alpha_{1A}$-ADR partial agonist as used herein does not exhibit agonist activity for other receptors including $\alpha_{1B}$-ADR or $\alpha_{1D}$-ADR receptors (for example in CHO cells expressing $\alpha_{1B}$-ADR or $\alpha_{1D}$-ADR using the methods described in Blue et al). In some embodiments a selective $\alpha_{1A}$-ADR agonist or a selective $\alpha_{1A}$-ADR partial agonist as used herein has a $pEC_{50}$ for $\alpha_{1B}$-ADR and $\alpha_{1D}$-ADR receptors that is less than 8.0; or less than 7.5; or less than 7.0; or less than 6.5; or less than 6.0; or less than 5.5; or less than 5; or less than 4.5; or less than 4; or less than 3.5; or between 2.5 and 6; or between 3 and 5.5; or between 3 and 5.0; or between 3 and 5. In some embodiments a selective $\alpha_{1A}$-ADR agonist or a selective $\alpha_{1A}$-ADR partial agonist as used herein has a $pEC_{50}$ for $\alpha_{1B}$-ADR and $\alpha_{1D}$-ADR receptors that is less than 7.0; or less than 6.5; or less than 6.0; or less than 5.5; or less than 5; or less than 4.5; or less than 4; or less than 3.5; or between 2.5 and 6; or between 3 and 5.5; or between 3 and 5.0; or between 3 and 5 using the InsPs accumulation assay described in Blue et al. (see, for example, Blue et al., Table 1 showing $pEC_{50}$ of >4.0 for RO 115-1240 (dabuzalgron) free base and HCl salt for $\alpha_{1B}$-ADR and $\alpha_{1D}$-ADR receptors in the InsPs accumulation assay). In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 7.0; or less than 6.5; or less than 6.0; or less than 5.5; or less than 5; or less than 4.5; or less than 4; or less than 3.5; or between 2.5 and 6; or between 3 and 5.5; or between 3 and 5.0; or between 3 and 5 using the FLIPR assay described in Blue et al (see, for example, Blue et al., Table 1 showing $pEC_{50}$ of >5.0 for RO 115-1240 (dabuzalgron) free base and HCl salt for $\alpha_{1B}$-AR and $\alpha_{1D}$-AR receptors in the FLIPR accumulation assay). In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of a non-selective agonist such as noradrenaline. In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of a non-selective agonist such as noradrenaline using the InsPs accumulation assay described in Blue et al. In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of a non-selective agonist such as noradrenaline using the FLIPR assay described in Blue et al. In some embodiments, a selective $\alpha_{1A}$-AR agonist or a selective $\alpha_{1A}$-AR partial agonist as used herein does not exhibit agonist activity for other receptors including $\alpha_{1B}$-AR or $\alpha_{1D}$-AR receptors (for example in CHO cells expressing $\alpha_{1B}$-AR or $\alpha_{1D}$-AR using the methods described in Blue et al.) at a concentration of 30 μMol/L or less; 50 μMol/L or less; 75 μMol/L or less; or 100 μMol/L or less. In some embodiments a selective $\alpha_{1A}$-AR agonist or a selective $\alpha_{1A}$-AR partial agonist does not bind to other receptors with a $pK_i$ higher than 5.5; or higher than 6.0; or higher than 6.5; or higher than 7.0; or higher than 7.2; or higher than 7.5; or higher than 7.8; or higher than 8.0; or higher than 9.0 (for example using methodologies described in Blue et al). In some embodiments a selective $\alpha_{1A}$-AR agonist or a selective $\alpha_{1A}$-AR partial agonist does not bind to $\alpha_{1B}$-AR or $\alpha_{1D}$-AR receptors with a $pK_i$ higher than 5.0; or higher than 5.5; or higher than 6.0; or higher than 7.0; or higher than 8.0; or higher than 9.0 (for example using methodologies described in Blue et al).

DETAILED DESCRIPTION OF THE INVENTION

In the following detailed description of the embodiments of the instant disclosure, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the instant disclosure.

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements. The term "about" will be understood by persons of ordinary skill in the art. Whether the term "about" is used explicitly or not, every quantity given herein refers to the actual given value, and it is also meant to refer to the approximation to such given value that would be reasonably inferred based on the ordinary skill in the art.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless indicated otherwise, the nomenclature of substituents that are not explicitly defined herein are arrived at by naming the terminal portion of the functionality followed by the adjacent functionality toward the point of attachment. A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. Such substituents can include, but are not limited to, $C_2$-$C_6$-alkenyl, $C_2$-$C_6$-alkynyl, halo, I, Br, Cl, F, OH, —COH, sulfhydryl, ($C_1$-$C_6$-alkyl)S—, $C_1$-$C_6$-alkylsulfinyl, nitro, cyano, trifluoromethyl, $NH_2$, =O, =S, =N—CN, =N—OH, —$OCH_2F$, —$OCHF_2$, —$OCF_3$, —$SCF_3$, —$SO_2$—$NH_2$, —$C_1$-$C_6$-alkoxy, —C(O)O—($C_1$-$C_6$ alkyl), —O—C(O)—($C_1$-$C_6$ alkyl), —C(O)—$NH_2$, —C(O)—N(H)—$C_1$-$C_6$ alkyl, —C(O)—N($C_1$-$C_6$ alkyl)$_2$, —OC(O)—

$NH_2$, —C(O)—H, —C(O)—($C_1$-$C_6$ alkyl), —C(S)—($C_1$-$C_6$ alkyl), —$NR^{70}R^{72}$, where $R^{70}$ and $R^{72}$ are each independently selected from H, $C_1$-$C_6$-alkyl, $C_2$-$C_6$-alkenyl, $C_2$-$C_6$-alkynyl, and C(O)—$C_1$-$C_6$-alkyl. As used herein, the term alkyl, unless otherwise stated, refers to both cyclic and noncyclic groups.

The term "haloalkyl" refers to a straight or branched chain alkyl group that is substituted with one or more halogen atoms (e.g., —$CHF_2$, —$CF_3$, —$CH_2CF_3$, etc.).

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Cycloalkyl groups can be substituted with groups such as those set out above for alkyl. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multi-cyclic ring systems include, but are not limited to, bicycle[4.4.0]decane, bicycle[2.2.1]heptane, spiro[2.2]pentane, and the like. (Cycloalkyl)oxy refers to —O-cycloalkyl. (Cycloalkyl)thio refers to —S-cycloalkyl. This term also encompasses oxidized forms of sulfur, such as —S(O)— cycloalkyl, or —$S(O)_2$-cycloalkyl.

Alkenyl groups refer to straight and branched chain and cycloalkyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Alkenyl groups can be substituted with groups such as those set out above for alkyl. Representative substituted alkenyl groups may be mono-substituted or substituted more than once, such as, but not limited to, mono-, di-, or tri-substituted. Examples of alkenyl groups include, but are not limited to, vinyl, allyl, —CH═CH($CH_3$), —CH═C($CH_3$)$_2$, —C($CH_3$)═$CH_2$, cyclopentenyl, cyclohexenyl, butadienyl, pentadienyl, and hexadienyl, among others.

Alkynyl groups refer to straight and branched chain and cycloalkyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Alkynyl groups can be substituted with groups such as those set out above for alkyl. Representative substituted alkynyl groups may be mono-substituted or substituted more than once, such as, but not limited to, mono-, di-, or tri-substituted. Exemplary alkynyl groups include, but are not limited to, ethynyl, propargyl, and —C≡C($CH_3$), among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Aryl groups can be substituted with groups such as those set out above for alkyl. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups. Aryloxy refers to —O-aryl. Arylthio refers to —S-aryl, wherein aryl is as defined herein. This term also encompasses oxidized forms of sulfur, such as —S(O)-aryl, or —$S(O)_2$-aryl. Heteroaryloxy refers to —O-heteroaryl. Heteroarylthio refers to —S-heteroaryl. This term also encompasses oxidized forms of sulfur, such as —S(O)-heteroaryl, or —$S(O)_2$-heteoaryl.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Heterocyclyl groups can be substituted with groups such as those set out above for alkyl. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups. Heterocyclyloxy refers to —O-heterocycyl. Heterocyclylthio refers to —S-heterocycyl. This term also encompasses oxidized forms of sulfur, such as —S(O)-heterocyclyl, or —$S(O)_2$-heterocyclyl.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Polycyclic groups can be substituted with groups such as those set out above for alkyl. Representative polycyclic groups may be substituted one or more times.

Halogen groups include F, Cl, Br, and I; nitro group refers to —$NO_2$; cyano group refers to —CN; isocyano group refers to —N—C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Alkoxy groups can be substituted with groups such as those set out above for alkyl. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

Thiol refers to —SH. Thiocarbonyl refers to (═S). Sulfonyl refers to —$SO_2$-halogen, —$SO_2$-alkyl, —$SO_2$-substituted alkyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclyl, and —$SO_2$-substituted heterocyclyl. Sulfonylamino refers to —$NR^aSO_2$-alkyl, —$NR^aSO_2$-substituted alkyl, —$NR^aSO_2$-cycloalkyl, —$NR^aSO_2$-substituted cycloalkyl, —$NR^aSO_2$-aryl, —$NR^aSO_2$-substituted aryl, —$NR^aSO_2$-heteroaryl, —$NR^aSO_2$-substituted heteroaryl, —$NR^aSO_2$-heterocyclyl, —$NR^aSO_2$-substituted heterocyclyl, wherein each $R^a$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl.

Carboxyl refers to —COOH or salts thereof. Carboxyester refers to —C(O)O-alkyl, —C(O)O— substituted alkyl, —C(O)O-aryl, —C(O)O-substituted aryl, —C(O)β-cycloalkyl, —C(O)O— substituted cycloalkyl, —C(O)O-heteroaryl, —C(O)O-substituted heteroaryl, —C(O)O— heterocyclyl, and —C(O)O-substituted heterocyclyl. (Carboxyester)amino refers to —$NR^a$—C(O)O-alkyl, —$NR^a$—C(O)O-substituted alkyl, —$NR^a$—C(O)O-aryl, —$NR^a$—C(O)O-substituted aryl, —$NR^a$—$C(O)_3$-cycloalkyl, —$NR^a$—C(O)O-substituted cycloalkyl, —$NR^a$—C(O)O-heteroaryl, —$NR^a$—C(O)O-substituted heteroaryl, —$NR^a$—C(O)O-heterocyclyl, and —$NR^a$—C(O)O-substituted heterocyclyl, wherein $R^a$ is as recited herein. (Carboxyester)oxy refers to —O—C(O)O-alkyl, —O—C(O)O— substituted alkyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclyl, and —O—C(O)O-substituted heterocyclyl. Oxo refers to (═O).

The terms "amine" and "amino" refer to derivatives of ammonia, wherein one of more hydrogen atoms have been replaced by a substituent which include, but are not limited to alkyl, alkenyl, aryl, and heterocyclyl groups. In some embodiments, substituted amino can include —NH—CO—R. Carbamate groups refers to —O(C═O)$NR_1R_2$, where $R_1$ and $R_2$ are independently hydrogen, aliphatic groups, aryl groups, or heterocyclyl groups.

Aminocarbonyl refers to —C(O)$N(R^b)_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen. Aminocarbonylalkyl refers to -alkylC(O)$N(R^b)_2$, wherein each $R^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each $R^b$ may optionally be joined together with the nitrogen bound thereto to form a heterocyclyl or substituted heterocyclyl group, provided that both $R^b$ are not both hydrogen. Aminocarbonylamino refers to —$NR^a$C(O)$N(R^b)_2$, wherein $R^a$ and each $R^b$ are as defined herein. Aminodicarbonylamino refers to —$NR^a$C(O)C(O)$N(R)_2$, wherein $R^a$ and each $R^b$ are as defined herein. Aminocarbonyloxy refers to —O—C(O)$N(R^b)_2$, wherein each $R^b$ independently is as defined herein. Aminosulfonyl refers to —$SO_2N(R^b)_2$, wherein each $R^b$ independently is as defined herein.

Imino refers to —N═$R^c$ wherein $R^c$ may be selected from hydrogen, aminocarbonylalkyloxy, substituted aminocarbonylalkyloxy, aminocarbonylalkylamino, and substituted aminocarbonylalkylamino.

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Prodrug" refers to a derivative of an active agent that requires a transformation within the body to release the active agent. In certain embodiments, the transformation is an enzymatic transformation. Prodrugs are frequently, although not necessarily, pharmacologically inactive or less active until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

Unless otherwise stated specifically by reciting an isotopically enriched atom (e.g., deuterium), structures as depicted herein are also meant to include compounds that differ only in the presence of one or more isotopically enriched atoms. For example, compounds having the present structures including the replacement of a hydrogen atom by deuterium or tritium, the replacement of a carbon atom by a $^{13}C$- or $^{14}C$-enriched carbon atom, the replacement of a fluorine atom by a $^{19}F$-enriched fluorine atom, etc., are within the scope of this disclosure.

Disclosed herein is a compound according to Formula (I) or an optically pure stereoisomer, pharmaceutically acceptable salt, solvate, or prodrug thereof.

Formula (I)

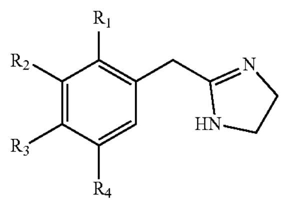

In some embodiments, $R_1$, $R_2$, $R_3$, and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments, $R_1$ and $R_2$ together with the C atoms to which they are attached optionally form an unsubstituted or substituted 5- to 8-membered heterocyclic ring having at least one nitrogen or oxygen atom, $R_2$ and $R_3$ together with the C atoms to which they are attached optionally form an unsubstituted or substituted 5- to 8-membered heterocyclic ring having at least one nitrogen or oxygen atom, or $R_3$ and $R_4$ together with the C atoms to which they are attached optionally form an unsubstituted or substituted 5- to 8-membered heterocyclic ring having at least one nitrogen or oxygen atom.

In some embodiments, at least two of $R_1$, $R_2$, $R_3$, and $R_4$ are not hydrogen if $R_1$ and $R_2$ together with the C atoms to which they are attached does not form an unsubstituted or substituted 5- to 8-membered heterocyclic ring having at least one nitrogen or oxygen atom, $R_2$ and $R_3$ together with the C atoms to which they are attached does not form an unsubstituted or substituted 5- to 8-membered heterocyclic ring having at least one nitrogen or oxygen atom, and $R_3$ and $R_4$ together with the C atoms to which they are attached does not form an unsubstituted or substituted 5- to 8-membered heterocyclic ring having at least one nitrogen or oxygen atom.

In some embodiments, $R_1$ and $R_2$ together with the C atoms to which they are attached optionally form an unsubstituted or substituted 5- to 6-membered heterocyclic ring having at least one nitrogen or oxygen atom, $R_2$ and $R_3$ together with the C atoms to which they are attached optionally form an unsubstituted or substituted 5- to 6-membered heterocyclic ring having at least one nitrogen or oxygen atom, or $R_3$ and $R_4$ together with the C atoms to which they are attached optionally form an unsubstituted or substituted 5- to 6-membered heterocyclic ring having at least one nitrogen or oxygen atom.

In some embodiments, at least two of $R_1$, $R_2$, $R_3$, and $R_4$ are not hydrogen if $R_1$ and $R_2$ together with the C atoms to which they are attached does not form an unsubstituted or substituted 5- to 6-membered heterocyclic ring having at least one nitrogen or oxygen atom, $R_2$ and $R_3$ together with the C atoms to which they are attached does not form an unsubstituted or substituted 5- to 6-membered heterocyclic ring having at least one nitrogen or oxygen atom, and $R_3$ and $R_4$ together with the C atoms to which they are attached does not form an unsubstituted or substituted 5- to 6-membered heterocyclic ring having at least one nitrogen or oxygen atom.

Also disclosed herein are compounds according to the structure of Formula Formula (I')

Formula (I')

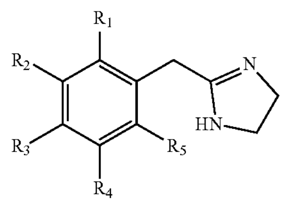

or pharmaceutically acceptable salt thereof, wherein:

$R_1$, $R_2$, $R_3$, $R_4$, and $R_5$ are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted cycloalkoxy, unsubstituted or substituted heterocycloalkyl, unsubstituted or substituted heterocycloalkoxy, unsubstituted or substituted aryl, and unsubstituted or substituted heteroaryl, or:

$R_1$ and $R_2$ together with the C atoms to which they are attached optionally form an unsubstituted or substituted 5- to 9-membered heterocyclic ring having at least one nitrogen or oxygen atom, $R_2$ and $R_3$ together with the C atoms to which they are attached optionally form an unsubstituted or substituted 5- to 9-membered heterocyclic ring having at least one nitrogen or oxygen atom, or $R_3$ and $R_4$ together with the C atoms to which they are attached optionally form an unsubstituted or substituted 5- to 9-membered heterocyclic ring having at least one nitrogen or oxygen atom, wherein at least two of $R_1$, $R_2$, $R_3$, $R_4$, and $R_5$ are not hydrogen.

In some embodiments, $R_1$, $R_2$, $R_3$, $R_4$, and $R_5$ are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted cycloalkoxy, unsubstituted or substituted heterocycloalkyl, unsubstituted or substituted heterocycloalkoxy, unsubstituted or substituted aryl, and unsubstituted or substituted heteroaryl.

In some embodiments, $R_1$ and $R_2$ together with the C atoms to which they are attached optionally form an unsubstituted or substituted 5- to 9-membered heterocyclic ring having at least one nitrogen or oxygen atom, $R_2$ and $R_3$ together with the C atoms to which they are attached optionally form an unsubstituted or substituted 5- to 9-membered heterocyclic ring having at least one nitrogen or oxygen atom, or $R_3$ and $R_4$ together with the C atoms to which they are attached optionally form an unsubstituted or substituted 5- to 9-membered heterocyclic ring having at least one nitrogen or oxygen atom.

In some embodiments, at least two of $R_1$, $R_2$, $R_3$, and $R_4$ are not hydrogen if $R_1$ and $R_2$ together with the C atoms to which they are attached does not form an unsubstituted or substituted 5- to 9-membered heterocyclic ring having at least one nitrogen or oxygen atom, $R_2$ and $R_3$ together with the C atoms to which they are attached does not form an unsubstituted or substituted 5- to 9-membered heterocyclic ring having at least one nitrogen or oxygen atom, and $R_3$ and $R_4$ together with the C atoms to which they are attached does not form an unsubstituted or substituted 5- to 9-membered heterocyclic ring having at least one nitrogen or oxygen atom.

Also disclosed herein are compounds according to the structure of Formula (I-a) or an optically pure stereoisomer, pharmaceutically acceptable salt, solvate, or prodrug thereof, wherein $R_1$, $R_2$, $R_3$, and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Formula (I-a)

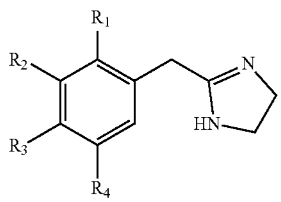

In some embodiments, at least two of $R_1$, $R_2$, $R_3$, and $R_4$ are not hydrogen.

Also disclosed herein are compounds according to the structure of Formula (I-a')

Formula (I-a')

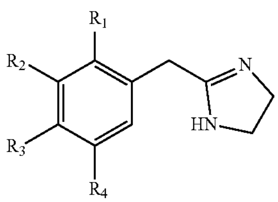

or pharmaceutically acceptable salt thereof, wherein:

$R_1$, $R_2$, $R_3$, and $R_4$ are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl, wherein at least two of $R_1$, $R_2$, $R_3$, and $R_4$ are not hydrogen.

Also disclosed herein is a compound according to Formula (I-b) or an optically pure stereoisomer, pharmaceutically acceptable salt, solvate, or prodrug thereof, wherein $R_1$ and $R_2$ together with the C atoms to which they are attached form an unsubstituted or substituted 5- to 8-membered heterocyclic ring having at least one nitrogen or oxygen atom.

Formula (I-b)

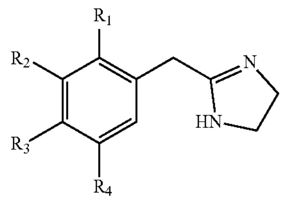

In some embodiments, $R_1$ and $R_2$ together with the C atoms to which they are attached form an unsubstituted or substituted 5-membered heterocyclic ring having at least one nitrogen or oxygen atom.

In some embodiments, $R_3$ and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein is a compound according to Formula (I-b')

Formula (I-b')

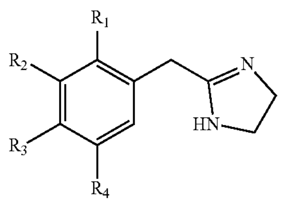

or pharmaceutically acceptable salt thereof, wherein:

$R_1$ and $R_2$ together with the C atoms to which they are attached form an unsubstituted or substituted 5- to 8-membered heterocyclic ring having at least one nitrogen or oxygen atom; and $R_3$ and $R_4$ are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments, $R_1$ and $R_2$ together with the C atoms to which they are attached form an unsubstituted or substituted 5-membered heterocyclic ring having at least one nitrogen or oxygen atom.

Also disclosed herein is a compound according to Formula (I-c) or an optically pure stereoisomer, pharmaceutically acceptable salt, solvate, or prodrug thereof, wherein $R_2$ and $R_3$ together with the C atoms to which they are attached form an unsubstituted or substituted 5- to 8-membered heterocyclic ring having at least one nitrogen or oxygen atom.

Formula (I-c)

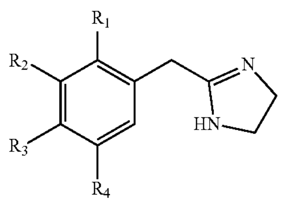

In some embodiments, $R_2$ and $R_3$ together with the C atoms to which they are attached form an unsubstituted or substituted 5-membered heterocyclic ring having at least one nitrogen or oxygen atom.

In some embodiments, $R_1$ and $R_4$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein is a compound according to Formula (I-c')

Formula (I-c')

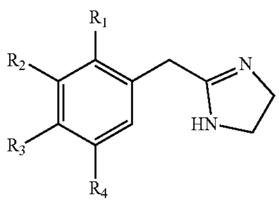

or pharmaceutically acceptable salt thereof, wherein:

$R_2$ and $R_3$ together with the C atoms to which they are attached form an unsubstituted or substituted 5- to 8-membered heterocyclic ring having at least one nitrogen or oxygen atom; and $R_1$ and $R_4$ are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments, $R_2$ and $R_3$ together with the C atoms to which they are attached form an unsubstituted or substituted 5-membered heterocyclic ring having at least one nitrogen or oxygen atom.

Also disclosed herein is a compound according to Formula (I-d) or an optically pure stereoisomer, pharmaceutically acceptable salt, solvate, or prodrug thereof, wherein $R_3$ and $R_4$ together with the C atoms to which they are attached form an unsubstituted or substituted 5- to 8-membered heterocyclic ring having at least one nitrogen or oxygen atom.

Formula (I-d)

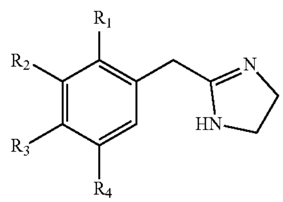

In some embodiments, $R_3$ and $R_4$ together with the C atoms to which they are attached form an unsubstituted or substituted 5-membered heterocyclic ring having at least one nitrogen or oxygen atom.

In some embodiments, $R_1$ and $R_2$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein is a compound according to Formula (I-d')

Formula (I-d')

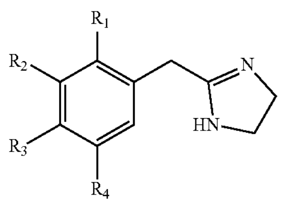

or pharmaceutically acceptable salt thereof, wherein:

$R_3$ and $R_4$ together with the C atoms to which they are attached form an unsubstituted or substituted 5- to 8-membered heterocyclic ring having at least one nitrogen or oxygen atom; and $R_1$ and $R_2$ are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments, $R_3$ and $R_4$ together with the C atoms to which they are attached form an unsubstituted or substituted 5-membered heterocyclic ring having at least one nitrogen or oxygen atom.

Also disclosed herein are compounds according an optically pure stereoisomer, pharmaceutically acceptable salt, solvate, or prodrug thereof.

Formula (II)

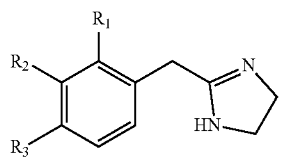

In some embodiments, $R_1$, $R_2$, and $R_3$, are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

In some embodiments, at least two of $R_1$, $R_2$, $R_3$, and $R_4$ are not hydrogen.

Also disclosed herein are compounds according to Formula (II')

Formula (II')

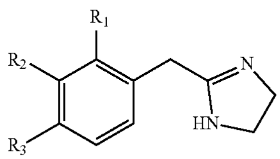

or pharmaceutically acceptable salt thereof, wherein:

$R_1$, $R_2$, and $R_3$, are independently selected from the group consisting of hydrogen, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl;

wherein at least two of $R_1$, $R_2$, and $R_3$ are not hydrogen.

Also disclosed herein are compounds according to the structure of Formula (III) or an optically pure stereoisomer, pharmaceutically acceptable salt, solvate, or prodrug thereof.

Formula (III)

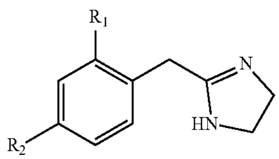

In some embodiments, $R_1$ and $R_2$ are independently selected from the group consisting of deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein are compounds according to the structure of Formula (III')

Formula (III')

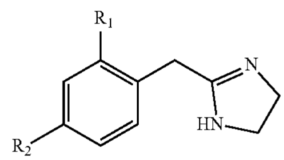

or pharmaceutically acceptable salt thereof wherein:

$R_1$ and $R_2$ are independently selected from the group consisting of halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein are compounds according to the structure of Formula (IV) or an optically pure stereoisomer, pharmaceutically acceptable salt, solvate, or prodrug thereof.

Formula (IV)

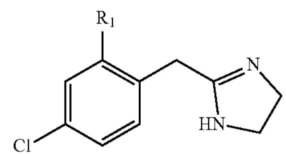

In some embodiments, $R_1$ is independently selected from the group consisting of deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein are compounds according to the structure of Formula (IV')

Formula (IV')

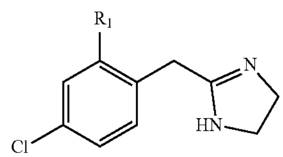

or pharmaceutically acceptable salt thereof, wherein:

$R_1$ is selected from the group consisting of halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted heterocycloalkyl, unsubstituted or substituted aryl, and unsubstituted or substituted heteroaryl.

Also disclosed herein are compounds according to the structure of Formula (I-e'):

Formula (I-e')

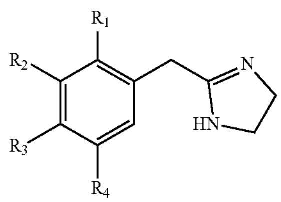

or pharmaceutically acceptable salt thereof, wherein:

$R_1$, $R_2$, $R_3$, and $R_4$ are independently selected from the group consisting of hydrogen, halogen, $C_{1-3}$alkyl, $C_{1-3}$haloalkyl, and $—OC_{1-3}$haloalkyl, wherein at least two of $R_1$, $R_2$, $R_3$, and $R_4$ are not hydrogen.

Also disclosed herein are compounds according to the structure of Formula (I-f):

Formula (I-f')

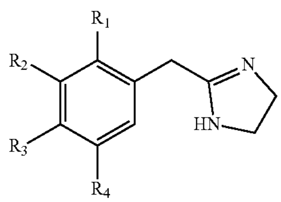

or pharmaceutically acceptable salt thereof, wherein:

$R_1$, $R_2$, $R_3$, and $R_4$ are independently selected from the group consisting of hydrogen, chloro, methyl, $—CF_3$, $—CH_2CF_3$, $—OCHF_2$, and $—OCF_3$, wherein at least two of $R_1$, $R_2$, $R_3$, and $R_4$ are not hydrogen.

Also disclosed herein are compounds according to the structure of Formula (I-g'):

Formula (I-g')

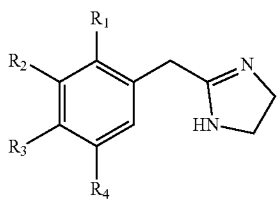

or pharmaceutically acceptable salt thereof, wherein:

$R_1$ is halogen, $C_{1-3}$alkyl, $C_{1-3}$haloalkyl, or $—OC_{1-3}$haloalkyl;

$R_2$ is hydrogen, $C_{1-3}$haloalkyl, or $—OC_{1-3}$haloalkyl;

$R_3$ is hydrogen, halogen, $C_{1-3}$alkyl, $C_{1-3}$haloalkyl, or $—OC_{1-3}$haloalkyl; and $R_4$ is hydrogen, $C_{1-3}$haloalkyl, or $—OC_{1-3}$haloalkyl, wherein at least one of $R_2$, $R_3$, and $R_4$ is not hydrogen.

Also disclosed herein are compounds according to the structure of Formula (I-h'):

Formula (I-h')

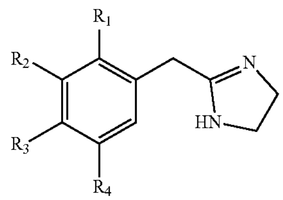

or pharmaceutically acceptable salt thereof, wherein:

$R_1$ is chloro, methyl, $—CHF_2$, $—CF_3$, $—CH_2CF_3$, $—OCHF_2$, or $—OCF_3$;

$R_2$ is hydrogen or $—CF_3$;

$R_3$ is hydrogen, chloro, methyl, $—CHF_2$, $—CF_3$, $—CH_2CF_3$, $—OCHF_2$, or $—OCF_3$; and $R_4$ is hydrogen or $—CF_3$, wherein at least one of $R_2$, $R_3$, and $R_4$ is not hydrogen.

Also disclosed herein are compounds according to the structure of Formula (I-i'):

Formula (I-i')

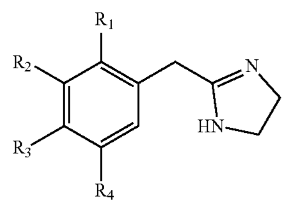

or pharmaceutically acceptable salt thereof, wherein:

$R_1$ is halogen, $C_{1-3}$alkyl, $C_{1-3}$haloalkyl, or $—OC_{1-3}$haloalkyl;

$R_2$ is hydrogen;

$R_3$ is halogen, $C_{1-3}$haloalkyl, or $—OC_{1-3}$haloalkyl; and $R_4$ is hydrogen.

Also disclosed herein are compounds according to the structure of Formula (I-j'):

Formula (I-j')

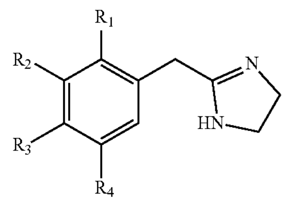

or pharmaceutically acceptable salt thereof, wherein:

$R_1$ is chloro, methyl, $—CHF_2$, $—CF_3$, $—CH_2CF_3$, $—OCHF_2$, or $—OCF_3$;

$R_2$ is hydrogen;

$R_3$ is chloro, $—CF_3$, or $—OCHF_2$; and $R_4$ is hydrogen.

As disclosed above and described herein, in some embodiments $R_1$, $R_2$, $R_3$, $R_4$, and $R_5$ are independently selected from the group consisting of hydrogen, deuterium, halogen, hydroxyl, cyano, nitro, unsubstituted or substituted sulfonyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted cycloalkoxy, unsubstituted or substituted heterocycloalkyl, unsubstituted or substituted heterocycloalkoxy, unsubstituted or substituted aryl, and unsubstituted or substituted heteroaryl.

In some embodiments, $R_1$ is hydrogen. In some embodiments, $R_1$ is deuterium. In some embodiments, $R_1$ is halogen. In some embodiments, $R_1$ is hydroxyl. In some embodiments, $R_1$ is cyano. In some embodiments, $R_1$ is nitro. In some embodiments, $R_1$ is unsubstituted or substituted sulfonyl. In some embodiments, $R_1$ is unsubstituted or substituted amino, unsubstituted or substituted alkyl. In some embodiments, $R_1$ is unsubstituted or substituted alkoxy. In some embodiments, $R_1$ is unsubstituted or substituted alkenyl. In some embodiments, $R_1$ is unsubstituted or substituted alkynyl. In some embodiments, $R_1$ is unsubstituted or substituted cycloalkyl. In some embodiments, $R_1$ is unsubstituted or substituted cycloalkoxy. In some embodiments, $R_1$ is unsubstituted or substituted heterocycloalkyl. In some embodiments, $R_1$ is unsubstituted or substituted heterocycloalkoxy. In some embodiments, $R_1$ is unsubstituted or substituted aryl. In some embodiments, $R_1$ is unsubstituted or substituted heteroaryl.

In some embodiments, $R_1$ is chloro. In some embodiments, $R_1$ is methyl. In some embodiments, $R_1$ is ethyl. In some embodiments, $R_1$ is isopropyl. In some embodiments, $R_1$ is cyclopropyl. In some embodiments, $R_1$ is t-butyl. In some embodiments, $R_1$ is cyclohexyl. In some embodiments, $R_1$ is phenyl. In some embodiments, $R_1$ is $—CFH_2$. In some embodiments, $R_1$ is $—CHF_2$. In some embodiments, $R_1$ is $—CHFCH_3$. In some embodiments, $R_1$ is $—CHOHCH_3$. In some embodiments, $R_1$ is $—CF_2CH_3$. In some embodiments, $R_1$ is $—CF_2Et$. In some embodiments, $R_1$ is $—CF_2iPr$. In some embodiments, $R_1$ is $—CF_3$. In some embodiments, $R_1$ is $—CH_2CF_3$. In some embodiments, $R_1$ is $—N(CH_3)CH_2CF_3$. In some embodiments, $R_1$ is —OMe. In some embodiments, $R_1$ is —OiPr. In some embodiments, $R_1$ is $—OCHF_2$. In some embodiments, $R_1$ is $—OCF_3$. In some embodiments, $R_1$ is $—CH_2OMe$. In some embodiments, $R_1$ is $—SO_2CF_3$. In some embodiments, $R_1$ is

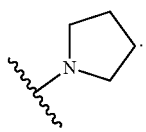

In some embodiments, $R_1$ is

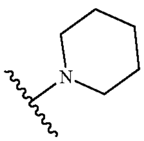

In some embodiments, $R_1$ is

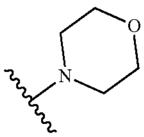

In some embodiments, $R_1$ is

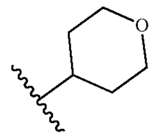

In some embodiments, $R_1$ is

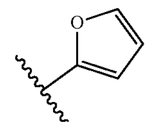

In some embodiments, $R_1$ is

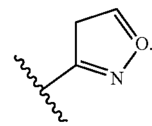

In some embodiments, $R_1$ is

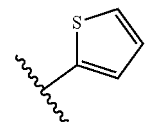

In some embodiments, $R_1$ is

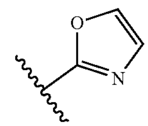

In some embodiments, $R_1$ is

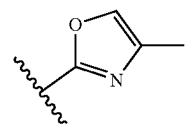

In some embodiments, $R_1$ is

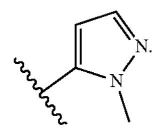 [SMILES: *c1ccnn1C]

In some embodiments, $R_1$ is

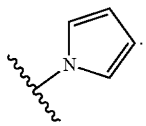

In some embodiments, $R_1$ is

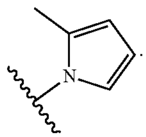 [SMILES: *n1cccc1C]

In some embodiments, $R_1$ is

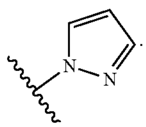 [SMILES: *n1cccn1]

In some embodiments, $R_1$ is

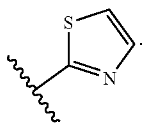

In some embodiments, $R_1$ is

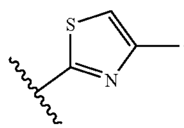

In some embodiments, $R_1$ is

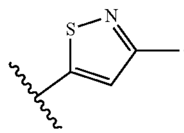

In some embodiments, $R_1$ is

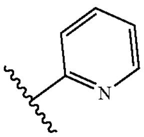

In some embodiments, $R_1$ is

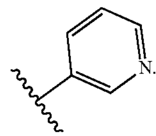 [SMILES: *c1cccnc1]

In some embodiments, $R_1$ is

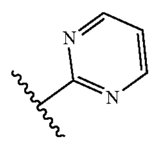

In some embodiments, $R_1$ is

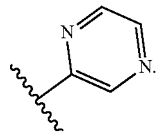 [SMILES: *c1cnccn1]

In some embodiments, $R_1$ is

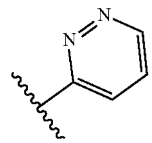

In some embodiments, $R_1$ is

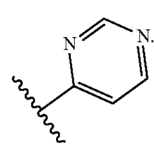 [SMILES: *c1ccncn1]

In some embodiments, $R_1$ is as depicted in the compounds of Table 1.

In some embodiments, $R_2$ is hydrogen. In some embodiments, $R_2$ is deuterium. In some embodiments, $R_2$ is halogen. In some embodiments, $R_2$ is hydroxyl. In some embodiments, $R_2$ is cyano. In some embodiments, $R_2$ is nitro. In some embodiments, $R_2$ is unsubstituted or substituted sulfonyl. In some embodiments, $R_2$ is unsubstituted or substituted amino, unsubstituted or substituted alkyl. In some embodiments, $R_2$ is unsubstituted or substituted alkoxy. In some embodiments, $R_2$ is unsubstituted or substituted alkenyl. In some embodiments, $R_2$ is unsubstituted or substituted alkynyl. In some embodiments, $R_2$ is unsubstituted or substituted cycloalkyl. In some embodiments, $R_2$ is unsubstituted or substituted cycloalkoxy. In some embodiments, $R_2$ is unsubstituted or substituted heterocycloalkyl. In some embodiments, $R_2$ is unsubstituted or substituted heterocycloalkoxy. In some embodiments, $R_2$ is unsubstituted or substituted aryl. In some embodiments, $R_2$ is unsubstituted or substituted heteroaryl.

In some embodiments, $R_2$ is chloro. In some embodiments, $R_2$ is methyl. In some embodiments, $R_2$ is ethyl. In some embodiments, $R_2$ is isopropyl. In some embodiments, $R_2$ is cyclopropyl. In some embodiments, $R_2$ is t-butyl. In some embodiments, $R_2$ is cyclohexyl. In some embodiments, $R_2$ is phenyl. In some embodiments, $R_2$ is $—CFH_2$. In some embodiments, $R_2$ is $—CHF_2$. In some embodiments, $R_2$ is $—CHFCH_3$. In some embodiments, $R_2$ is $—CHOHCH_3$. In some embodiments, $R_2$ is $—CF_2CH_3$. In some embodiments, $R_2$ is $—CF_2Et$. In some embodiments, $R_2$ is $—CF_2iPr$. In some embodiments, $R_2$ is $—CF_3$. In some embodiments, $R_2$ is $—CH_2CF_3$. In some embodiments, $R_2$ is $—N(CH_3)CH_2CF_3$. In some embodiments, $R_2$ is —OMe. In some embodiments, $R_2$ is —OiPr. In some embodiments, $R_2$ is $—OCHF_2$. In some embodiments, $R_2$ is $—OCF_3$. In some embodiments, $R_2$ is $—CH_2OMe$. In some embodiments, $R_2$ is $—SO_2CF_3$. In some embodiments, $R_2$ is

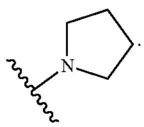 [SMILES: *N1CCCC1]

In some embodiments, $R_2$ is

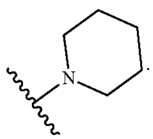 [SMILES: *N1CCCCC1]

In some embodiments, $R_2$ is

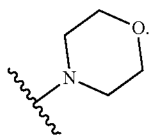

In some embodiments, $R_2$ is

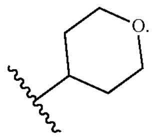 [SMILES: *C1CCOCC1]

In some embodiments, $R_2$ is

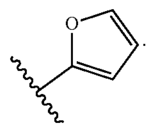

In some embodiments, $R_2$ is

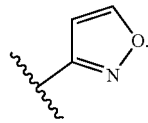 [SMILES: *c1ccon1]

In some embodiments, $R_2$ is

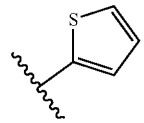

In some embodiments, $R_2$ is

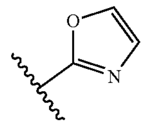

In some embodiments, $R_2$ is

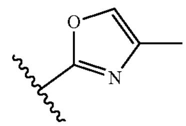

In some embodiments, $R_2$ is

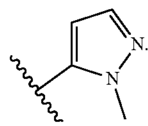 [SMILES: *c1ccnn1C]

In some embodiments, $R_2$ is

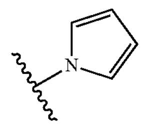

In some embodiments, $R_2$ is

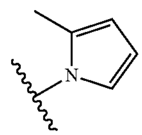

In some embodiments, $R_2$ is

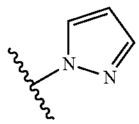

In some embodiments, $R_2$ is

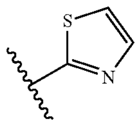

In some embodiments, $R_2$ is

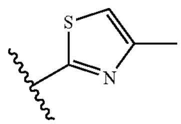

In some embodiments, $R_2$ is

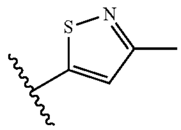

In some embodiments, $R_2$ is

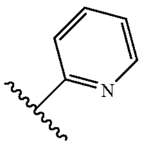

In some embodiments, $R_2$ is

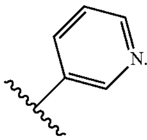 [SMILES: *c1cccnc1]

In some embodiments, $R_2$ is

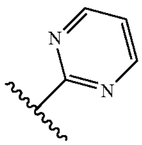

In some embodiments, $R_2$ is

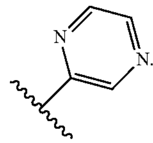 [SMILES: *c1cnccn1]

In some embodiments, $R_2$ is

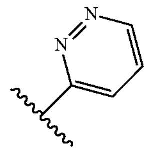

In some embodiments, $R_2$ is

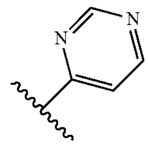

In some embodiments, $R_2$ is as depicted in the compounds of Table 1.

In some embodiments, $R_3$ is hydrogen. In some embodiments, $R_3$ is deuterium. In some embodiments, $R_3$ is halogen. In some embodiments, $R_3$ is hydroxyl. In some embodiments, $R_3$ is cyano. In some embodiments, $R_3$ is nitro. In some embodiments, $R_3$ is unsubstituted or substituted sulfonyl. In some embodiments, $R_3$ is unsubstituted or substituted amino, unsubstituted or substituted alkyl. In some embodiments, $R_3$ is unsubstituted or substituted alkoxy. In some embodiments, $R_3$ is unsubstituted or substituted alkenyl. In some embodiments, $R_3$ is unsubstituted or substituted alkynyl. In some embodiments, $R_3$ is unsubstituted or substituted cycloalkyl. In some embodiments, $R_3$ is unsubstituted or substituted cycloalkoxy. In some embodiments, $R_3$ is unsubstituted or substituted heterocycloalkyl. In some embodiments, $R_3$ is unsubstituted or substituted heterocycloalkoxy. In some embodiments, $R_3$ is unsubstituted or substituted aryl. In some embodiments, $R_3$ is unsubstituted or substituted heteroaryl.

In some embodiments, $R_3$ is chloro. In some embodiments, $R_3$ is methyl. In some embodiments, $R_3$ is ethyl. In some embodiments, $R_3$ is isopropyl. In some embodiments, $R_3$ is cyclopropyl. In some embodiments, $R_3$ is t-butyl. In some embodiments, $R_3$ is cyclohexyl. In some embodiments, $R_3$ is phenyl. In some embodiments, $R_3$ is $-CFH_2$. In some embodiments, $R_3$ is $-CHF_2$. In some embodiments, $R_3$ is $-CHFCH_3$. In some embodiments, $R_3$ is $-CHOHCH_3$. In some embodiments, $R_3$ is $-CF_2CH_3$. In some embodiments, $R_3$ is $-CF_2Et$. In some embodiments, $R_3$ is $-CF_2iPr$. In some embodiments, $R_3$ is $-CF_3$. In some embodiments, $R_3$ is $-CH_2CF_3$. In some embodiments, $R_3$ is $-N(CH_3)CH_2CF_3$. In some embodiments, $R_3$ is $-OMe$. In some embodiments, $R_3$ is $-OiPr$. In some embodiments, $R_3$ is $-OCHF_2$. In some embodiments, $R_3$ is $-OCF_3$. In some embodiments, $R_3$ is $-CH_2OMe$. In some embodiments, $R_3$ is $-SO_2CF_3$. In some embodiments, $R_3$ is

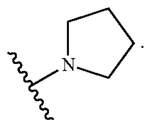 [SMILES: *N1CCCC1]
In some embodiments, $R_3$ is
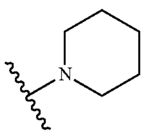
In some embodiments, $R_3$ is
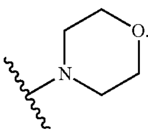 [SMILES: *N1CCOCC1]
In some embodiments, $R_3$ is
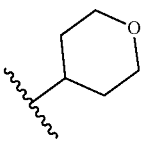
In some embodiments, $R_3$ is
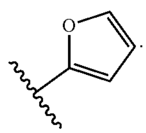
In some embodiments, $R_3$ is
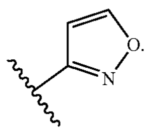 [SMILES: *c1ccon1]
In some embodiments, $R_3$ is
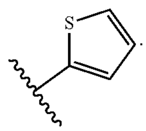
In some embodiments, $R_3$ is
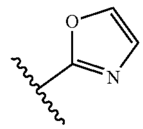
In some embodiments, $R_3$ is
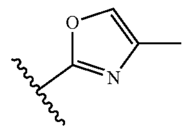
In some embodiments, $R_3$ is
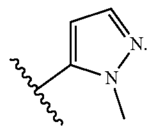 [SMILES: *c1ccnn1C]
In some embodiments, $R_3$ is
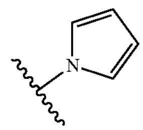
In some embodiments, $R_3$ is
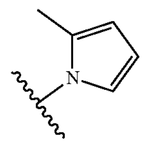
In some embodiments, $R_3$ is
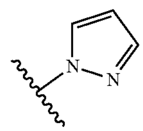
In some embodiments, $R_3$ is
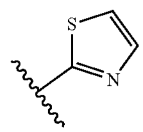

In some embodiments, $R_3$ is

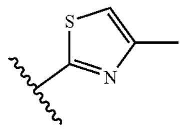

In some embodiments, $R_3$ is

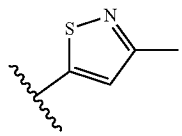

In some embodiments, $R_3$ is

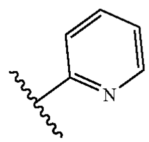

In some embodiments, $R_3$ is

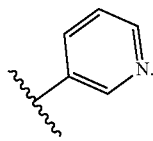 [SMILES: *c1cccnc1]

In some embodiments, $R_3$ is

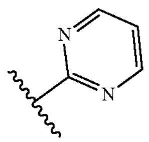

In some embodiments, $R_3$ is

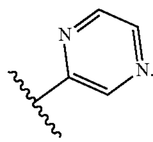 [SMILES: *c1cnccn1]

In some embodiments, $R_3$ is

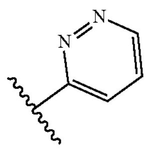

In some embodiments, $R_3$ is

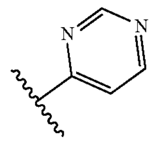

In some embodiments, $R_3$ is as depicted in the compounds of Table 1.

In some embodiments, $R_4$ is hydrogen. In some embodiments, $R_4$ is deuterium. In some embodiments, $R_4$ is halogen. In some embodiments, $R_4$ is hydroxyl. In some embodiments, $R_4$ is cyano. In some embodiments, $R_4$ is nitro. In some embodiments, $R_4$ is unsubstituted or substituted sulfonyl. In some embodiments, $R_4$ is unsubstituted or substituted amino, unsubstituted or substituted alkyl. In some embodiments, $R_4$ is unsubstituted or substituted alkoxy. In some embodiments, $R_4$ is unsubstituted or substituted alkenyl. In some embodiments, $R_4$ is unsubstituted or substituted alkynyl. In some embodiments, $R_4$ is unsubstituted or substituted cycloalkyl. In some embodiments, $R_4$ is unsubstituted or substituted cycloalkoxy. In some embodiments, $R_4$ is unsubstituted or substituted heterocycloalkyl. In some embodiments, $R_4$ is unsubstituted or substituted heterocycloalkoxy. In some embodiments, $R_4$ is unsubstituted or substituted aryl. In some embodiments, $R_4$ is unsubstituted or substituted heteroaryl.

In some embodiments, $R_4$ is chloro. In some embodiments, $R_4$ is methyl. In some embodiments, $R_4$ is ethyl. In some embodiments, $R_4$ is isopropyl. In some embodiments, $R_4$ is cyclopropyl. In some embodiments, $R_4$ is t-butyl. In some embodiments, $R_4$ is cyclohexyl. In some embodiments, $R_4$ is phenyl. In some embodiments, $R_4$ is $-CFH_2$. In some embodiments, $R_4$ is $-CHF_2$. In some embodiments, $R_4$ is $-CHFCH_3$. In some embodiments, $R_4$ is $-CHOHCH_3$. In some embodiments, $R_4$ is $-CF_2CH_3$. In some embodiments, $R_4$ is $-CF_2Et$. In some embodiments, $R_4$ is $-CF_2iPr$. In some embodiments, $R_4$ is $-CF_3$. In some embodiments, $R_4$ is $-CH_2CF_3$. In some embodiments, $R_4$ is $-N(CH_3)CH_2CF_3$. In some embodiments, $R_4$ is $-OMe$. In some embodiments, $R_4$ is $-OiPr$. In some embodiments, $R_4$ is $-OCHF_2$. In some embodiments, $R_4$ is $-OCF_3$. In some embodiments, $R_4$ is $-CH_2OMe$. In some embodiments, $R_4$ is $-SO_2CF_3$. In some embodiments, $R_4$ is

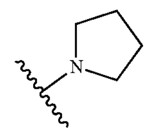

In some embodiments, $R_4$ is

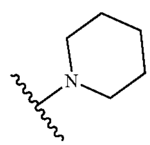

In some embodiments, $R_4$ is

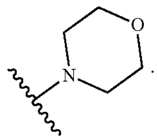 [SMILES: *N1CCOCC1]

In some embodiments, $R_4$ is

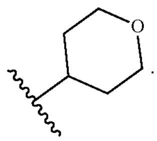 [SMILES: *C1CCOCC1]

In some embodiments, $R_4$ is

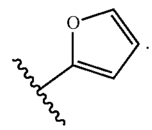

In some embodiments, $R_4$ is

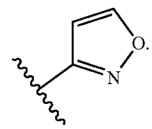 [SMILES: *c1ccon1]

In some embodiments, $R_4$ is

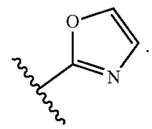 [SMILES: *c1ncco1]

In some embodiments, $R_4$ is

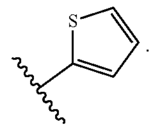 [SMILES: *c1cccs1]

In some embodiments, $R_4$ is

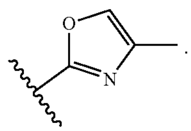 [SMILES: *c1nc(C)co1]

In some embodiments, $R_4$ is

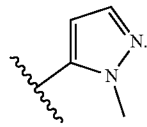 [SMILES: *c1ccnn1C]

In some embodiments, $R_4$ is

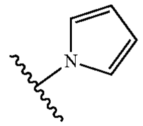

In some embodiments, $R_4$ is

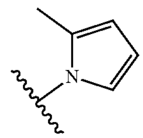

In some embodiments, $R_4$ is

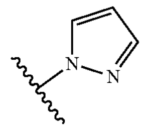

In some embodiments, $R_4$ is

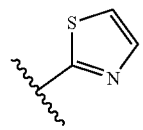

In some embodiments, $R_4$ is

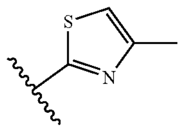

In some embodiments, $R_4$ is

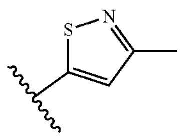

In some embodiments, $R_4$ is

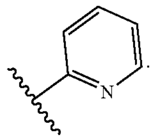 [SMILES: *c1ccccn1]

In some embodiments, $R_4$ is

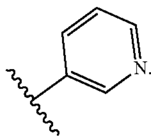 [SMILES: *c1cccnc1]

In some embodiments, $R_4$ is

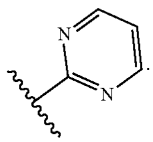 [SMILES: *c1ncccn1]

In some embodiments, $R_4$ is

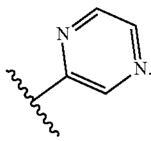 [SMILES: *c1cnccn1]

In some embodiments, $R_4$ is

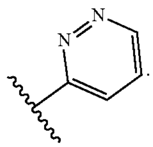 [SMILES: *c1cccnn1]

In some embodiments, $R_4$ is

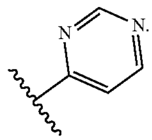 [SMILES: *c1ccncn1]

In some embodiments, $R_4$ is as depicted in the compounds of Table 1.

In some embodiments, $R_5$ is hydrogen. In some embodiments, $R_5$ is deuterium. In some embodiments, $R_5$ is halogen. In some embodiments, $R_5$ is hydroxyl. In some embodiments, $R_5$ is cyano. In some embodiments, $R_5$ is nitro. In some embodiments, $R_5$ is unsubstituted or substituted sulfonyl. In some embodiments, $R_5$ is unsubstituted or substituted amino, unsubstituted or substituted alkyl. In some embodiments, $R_5$ is unsubstituted or substituted alkoxy. In some embodiments, $R_5$ is unsubstituted or substituted alkenyl. In some embodiments, $R_5$ is unsubstituted or substituted alkynyl. In some embodiments, $R_5$ is unsubstituted or substituted cycloalkyl. In some embodiments, $R_5$ is unsubstituted or substituted cycloalkoxy. In some embodiments, $R_5$ is unsubstituted or substituted heterocycloalkyl. In some embodiments, $R_5$ is unsubstituted or substituted heterocycloalkoxy. In some embodiments, $R_5$ is unsubstituted or substituted aryl. In some embodiments, $R_5$ is unsubstituted or substituted heteroaryl.

In some embodiments, $R_5$ is chloro. In some embodiments, $R_5$ is methyl. In some embodiments, $R_5$ is ethyl. In some embodiments, $R_5$ is isopropyl. In some embodiments, $R_5$ is cyclopropyl. In some embodiments, $R_5$ is t-butyl. In some embodiments, $R_5$ is cyclohexyl. In some embodiments, $R_5$ is phenyl. In some embodiments, $R_5$ is $—CFH_2$. In some embodiments, $R_5$ is $—CHF_2$. In some embodiments, $R_5$ is $—CHFCH_3$. In some embodiments, $R_5$ is $—CHOHCH_3$. In some embodiments, $R_5$ is $—CF_2CH_3$. In some embodiments, $R_5$ is $—CF_2Et$. In some embodiments, $R_5$ is $—CF_2iPr$. In some embodiments, $R_5$ is $—CF_3$. In some embodiments, $R_5$ is $—CH_2CF_3$. In some embodiments, $R_5$ is $—N(CH_3)CH_2CF_3$. In some embodiments, $R_5$ is —OMe. In some embodiments, $R_5$ is —OiPr. In some embodiments, $R_5$ is $—OCHF_2$. In some embodiments, $R_5$ is $—OCF_3$. In some embodiments, $R_5$ is $—CH_2OMe$. In some embodiments, $R_5$ is $—SO_2CF_3$. In some embodiments, $R_5$ is

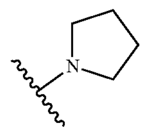

In some embodiments, $R_5$ is

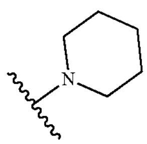

In some embodiments, $R_5$ is

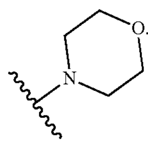 [SMILES: *N1CCOCC1]

In some embodiments, $R_5$ is

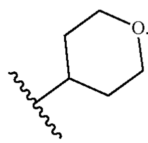 [SMILES: *C1CCOCC1]

In some embodiments, $R_5$ is

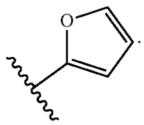

In some embodiments, $R_5$ is

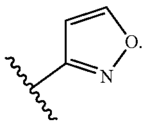 [SMILES: *c1ccon1]

In some embodiments, $R_5$ is

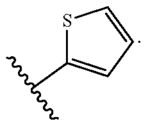

In some embodiments, $R_5$ is

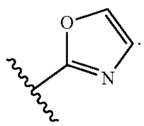

In some embodiments, $R_5$ is

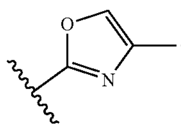

In some embodiments, $R_5$ is

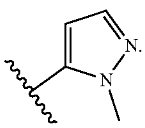 [SMILES: *c1ccnn1C]

In some embodiments, $R_5$ is

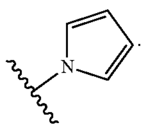 [SMILES: *n1cccc1]

In some embodiments, $R_5$ is

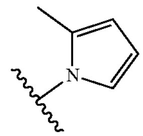

In some embodiments, $R_5$ is

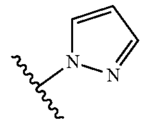

In some embodiments, $R_5$ is

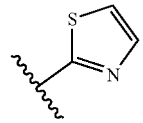

In some embodiments, $R_5$ is

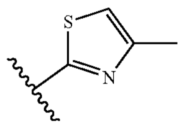

In some embodiments, $R_5$ is

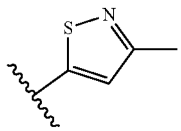

In some embodiments, $R_5$ is

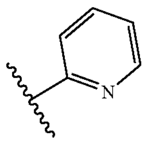

In some embodiments, $R_5$ is

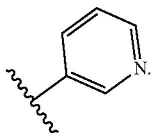 [SMILES: *c1cccnc1]

In some embodiments, $R_5$ is

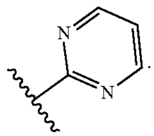 [SMILES: *c1ncccn1]

In some embodiments, $R_5$ is

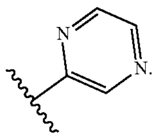 [SMILES: *c1cnccn1]

In some embodiments, $R_5$ is

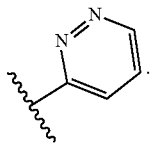 [SMILES: *c1cccnn1]

In some embodiments, $R_5$ is

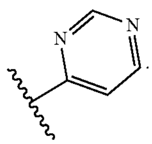 [SMILES: *c1ccncn1]

In some embodiments, $R_5$ is as depicted in the compounds of Table 1.

In some embodiments, $R_1$ and $R_2$ together with the C atoms to which they are attached optionally form an unsubstituted or substituted 5- to 9-membered heterocyclic ring having at least one nitrogen or oxygen atom.

In some embodiments, $R_1$ and $R_2$ come together to form

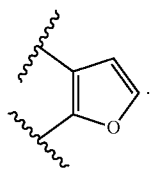 [SMILES: *c1ccoc1*]

In some embodiments, $R_1$ and $R_2$ come together to form

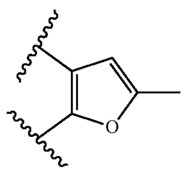

In some embodiments, $R_1$ and $R_2$ come together to form

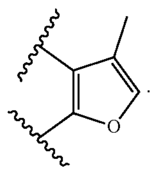 [SMILES: *c1occ(C)c1*]

In some embodiments, $R_1$ and $R_2$ come together to form

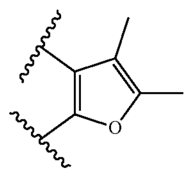

In some embodiments, $R_1$ and $R_2$ come together to form

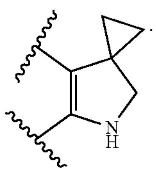 [SMILES: *C1=C(*)C2(CC2)CN1]

In some embodiments, $R_1$ and $R_2$ come together to form

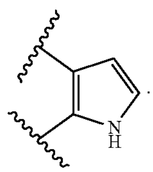 [SMILES: *c1cc[nH]c1*]

In some embodiments, $R_1$ and $R_2$ come together to form

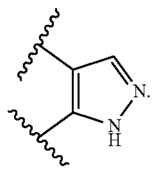 [SMILES: *c1cn[nH]c1*]

In some embodiments, $R_1$ and $R_2$ come together to form

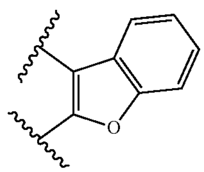

In some embodiments, $R_1$ and $R_2$ come together as depicted in the compounds of Table 1.

In some embodiments, $R_2$ and $R_3$ together with the C atoms to which they are attached optionally form an unsubstituted or substituted 5- to 9-membered heterocyclic ring having at least one nitrogen or oxygen atom.

In some embodiments, $R_2$ and $R_3$ come together to form

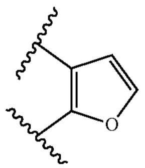

In some embodiments, $R_2$ and $R_3$ come together to form

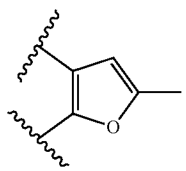

In some embodiments, $R_2$ and $R_3$ come together to form

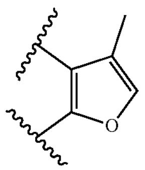

In some embodiments, $R_2$ and $R_3$ come together to form

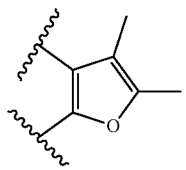

In some embodiments, $R_2$ and $R_3$ come together to form

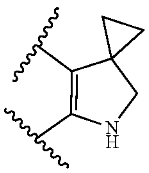

In some embodiments, $R_2$ and $R_3$ come together to form

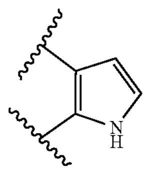

In some embodiments, $R_2$ and $R_3$ come together to form

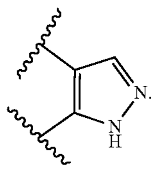 [SMILES: *c1cn[nH]c1*]

In some embodiments, $R_2$ and $R_3$ come together to form

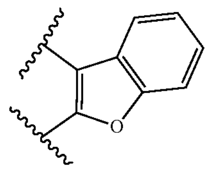

In some embodiments, $R_2$ and $R_3$ come together as depicted in the compounds of Table 1.

In some embodiments, $R_3$ and $R_4$ together with the C atoms to which they are attached optionally form an unsubstituted or substituted 5- to 9-membered heterocyclic ring having at least one nitrogen or oxygen atom.

In some embodiments, $R_3$ and $R_4$ come together to form

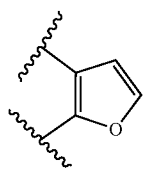

In some embodiments, $R_3$ and $R_4$ come together to form

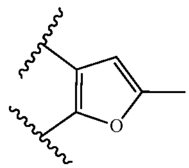

In some embodiments, $R_3$ and $R_4$ come together to form

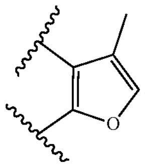

In some embodiments, $R_3$ and $R_4$ come together to form

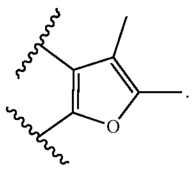 [SMILES: *c1oc(C)c(C)c1*]

In some embodiments, $R_3$ and $R_4$ come together to form

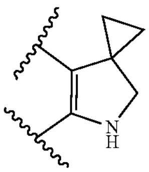

In some embodiments, $R_3$ and $R_4$ come together to form

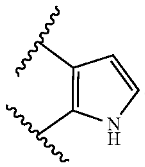

In some embodiments, $R_3$ and $R_4$ come together to form

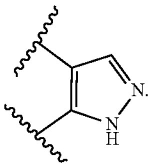

In some embodiments, $R_3$ and $R_4$ come together to form

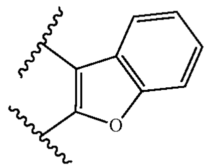

In some embodiments, $R_3$ and $R_4$ come together as depicted in the compounds of Table 1.

In some embodiments, at least two of $R_1$, $R_2$, $R_3$, and $R_4$ are not hydrogen if $R_1$ and $R_2$ together with the C atoms to which they are attached do not form an unsubstituted or substituted 5- to 8-membered heterocyclic ring having at least one nitrogen or oxygen atom.

As disclosed above and described herein, in some embodiments $R_1$, $R_2$, $R_3$, and $R_4$ are independently hydrogen, halogen, $C_{1-3}$alkyl, $C_{1-3}$haloalkyl, —$OC_{1-3}$alkyl, or —$OC_{1-3}$haloalkyl (e.g., fluoro, chloro, methyl, —$CHF_2$, —$CF_3$, —$CH_2CF_3$, —$OCHF_2$, —$OCF_3$. etc.).

In some embodiments, $R_1$ is hydrogen. In some embodiments, $R_1$ is halogen. In some embodiments, $R_1$ is $C_{1-3}$alkyl. In some embodiments, $R_1$ is $C_{1-3}$haloalkyl. In some embodiments, $R_1$ is —$OC_{1-3}$alkyl. In some embodiments, $R_1$ is —$OC_{1-3}$haloalkyl. In some embodiments, $R_1$ is fluoro. In some embodiments, $R_1$ is chloro. In some embodiments, $R_1$ is methyl. In some embodiments, $R_1$ is ethyl. In some embodiments, $R_1$ is —$CHF_2$. In some embodiments, $R_1$ is —$CF_3$. In some embodiments, $R_1$ is —$CH_2CF_3$. In some embodiments, $R_1$ is —$OCHF_2$. In some embodiments, $R_1$ is —$OCF_3$.

In some embodiments, $R_2$ is hydrogen. In some embodiments, $R_2$ is halogen. In some embodiments, $R_2$ is $C_{1-3}$alkyl. In some embodiments, $R_2$ is $C_{1-3}$haloalkyl. In some embodiments, $R_2$ is —$OC_{1-3}$alkyl. In some embodiments, $R_2$ is —$OC_{1-3}$haloalkyl. In some embodiments, $R_2$ is fluoro. In some embodiments, $R_2$ is chloro. In some embodiments, $R_2$ is methyl. In some embodiments, $R_2$ is ethyl. In some embodiments, $R_2$ is —$CHF_2$. In some embodiments, $R_2$ is —$CF_3$. In some embodiments, $R_2$ is —$CH_2CF_3$. In some embodiments, $R_2$ is —$OCHF_2$. In some embodiments, $R_2$ is —$OCF_3$.

In some embodiments, $R_3$ is hydrogen. In some embodiments, $R_3$ is halogen. In some embodiments, $R_3$ is $C_{1-3}$alkyl. In some embodiments, $R_3$ is $C_{1-3}$haloalkyl. In some embodiments, $R_3$ is —$OC_{1-3}$alkyl. In some embodiments, $R_3$ is —$OC_{1-3}$haloalkyl. In some embodiments, $R_3$ is fluoro. In some embodiments, $R_3$ is chloro. In some embodiments, $R_3$ is methyl. In some embodiments, $R_3$ is ethyl. In some embodiments, $R_3$ is —$CHF_2$. In some embodiments, $R_3$ is —$CF_3$. In some embodiments, $R_3$ is —$CH_2CF_3$. In some embodiments, $R_3$ is —$OCHF_2$. In some embodiments, $R_3$ is —$OCF_3$.

In some embodiments, $R_4$ is hydrogen. In some embodiments, $R_4$ is halogen. In some embodiments, $R_4$ is $C_{1-3}$alkyl. In some embodiments, $R_4$ is $C_{1-3}$haloalkyl. In some embodiments, $R_4$ is —$OC_{1-3}$alkyl. In some embodiments, $R_4$ is —$OC_{1-3}$haloalkyl. In some embodiments, $R_4$ is fluoro. In some embodiments, $R_4$ is chloro. In some embodiments, $R_4$ is methyl. In some embodiments, $R_4$ is ethyl. In some embodiments, $R_4$ is —$CHF_2$. In some embodiments, $R_4$ is —$CF_3$. In some embodiments, $R_4$ is —$CH_2CF_3$. In some embodiments, $R_4$ is —$OCHF_2$. In some embodiments, $R_4$ is —$OCF_3$.

In some embodiments, $R_1$, $R_2$, $R_3$, and $R_4$ are as depicted in the compounds of Table 1.

In some embodiments a compound as disclosed herein is an agonist, partial agonist or antagonist of an adrenergic receptor; in some embodiments the compound is an $\alpha_{1A}$-adrenergic receptor agonist; in some embodiments the compound is an $\alpha_{1A}$-adrenergic receptor partial agonist; in some embodiments the compound is an $\alpha_{1A}$-adrenergic receptor antagonist.

Further disclosed is a method of treating a subject with a disease, the method including administering to the subject a therapeutically effective amount of a compound as disclosed herein, i.e., a compound with a structure of Formula (I), Formula (I'), Formula (I-a), Formula (I-a'), Formula (I-b), Formula (I-b'), Formula (I-c), Formula (I-c'), Formula (I-d), Formula (I-d'), Formula (I-e'), Formula (I-f'), Formula (I-g'), Formula (I-h'), Formula (I-i'), Formula (I-j'), Formula (II), Formula (II'), Formula (III), Formula (III'), Formula (IV), or Formula (IV'). In some embodiments, the disease is a disease associated with an adrenergic receptor. In some embodiments, the disease is a neurodegenerative disease. In some embodiments, the subject is a human.

In some embodiments, the disease is selected from myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, and neuronal ceroid lipofuscinosis. In some embodiments, the compound is administered to the subject through oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route.

In some embodiments, the disease is a neurodegenerative disease that is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CID etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS). In some embodiments the disease is a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder). In some embodiments the subject does not have Alzheimer's disease (AD). In some embodiments the subject does not have Down Syndrome.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those at risk or needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. In some embodiments, such amount should be sufficient to modulate an adrenergic receptor.

In some embodiments, an effective amount of an adrenergic receptor modulating compound is an amount that ranges from about 50 ng/ml to 50 pg/ml (e.g., from about 50 ng/ml to 40 pg/ml, from about 30 ng/ml to 20 pg/ml, from about 50 ng/ml to 10 μg/ml, from about 50 ng/ml to 1 μg/ml, from about 50 ng/ml to 800 ng/ml, from about 50 ng/ml to 700 ng/ml, from about 50 ng/ml to 600 ng/ml, from about 50 ng/ml to 500 ng/ml, from about 50 ng/ml to 400 ng/ml, from about 60 ng/ml to 400 ng/ml, from about 70 ng/ml to 300 ng/ml, from about 60 ng/ml to 100 ng/ml, from about 65 ng/ml to 85 ng/ml, from about 70 ng/ml to 90 ng/ml, from about 200 ng/ml to 900 ng/ml, from about 200 ng/ml to 800 ng/ml, from about 200 ng/ml to 700 ng/ml, from about 200 ng/ml to 600 ng/ml, from about 200 ng/ml to 500 ng/ml, from about 200 ng/ml to 400 ng/ml, or from about 200 ng/ml to about ng/ml).

In some embodiments, an effective amount of an adrenergic receptor modulating compound is an amount that ranges from about 10 pg to 100 mg, e.g., from about 10 pg to 50 pg, from about 50 pg to 150 pg, from about 150 pg to 250 pg, from about 250 pg to 500 pg, from about 500 pg to 750 pg, from about 750 pg to 1 ng, from about 1 ng to 10 ng, from about 10 ng to 50 ng, from about 50 ng to 150 ng, from about 150 ng to 250 ng, from about 250 ng to 500 ng, from about 500 ng to 750 ng, from about 750 ng to 1 mg, from about 1 pg to 10 pg, from about 10 pg to 50 pg, from about 50 pg to 150 pg, from about 150 pg to 250 pg, from about 250 pg to 500 pg, from about 500 pg to 750 pg, from about 750 pg to 1 mg, from about 1 mg to 50 mg, from about 1 mg to 100 mg, or from about 50 mg to 100 mg. The amount can be a single dose amount or can be a total daily amount. The total daily amount can range from about 10 pg to 100 mg, or can range from about 100 mg to 500 mg, or can range from about 500 mg to 1000 mg.

Also disclosed herein is a pharmaceutical composition including a compound as disclosed herein, i.e., a compound with a structure of Formula (I), Formula (I'), Formula (I-a), Formula (I-a'), Formula (I-b), Formula (I-b'), Formula (I-c), Formula (I-c'), Formula (I-d), Formula (I-d'), Formula (I-e'), Formula (I-f'), Formula (I-g'), Formula (I-h'), Formula (I-i'), Formula (I-j'), Formula (II), Formula (II'), Formula (III), Formula (III'), Formula (IV), or Formula (IV') and a pharmaceutically acceptable excipient.

The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

In some embodiments, a compound as disclosed herein may be an adrenergic receptor modulating compound (e.g., an agonist, partial agonist or antagonist of an adrenergic receptor). The adrenergic receptor modulating compounds of the present disclosure can in some embodiments find use in modulating the activity of a target adrenergic receptor in vitro or in vivo. Aspects of the subject methods include contacting a sample with an effective amount of an adrenergic receptor modulating compound (e.g., as described herein) to determine whether the activity desired exists.

Adrenergic receptors (ADRs) are G-protein coupled receptors (GPCR) that are widely expressed throughout the body and play an important role in regulating multiple physiological processes including cognition, stress-related behavior, inflammation, and smooth muscle contraction/dilation, cardiac muscle contraction, airway reactivity and cognition. Adrenergic receptors mediate the central and peripheral effects of noradrenaline (NA) and adrenaline. Multiple subtypes of ADRs exist, including $\alpha$-adrenergic receptors and 3-adrenergic receptors. Each subtype is expressed in distinct patterns and involved in different physiological processes. Therefore, ligands that selectively target one subtype are valuable both as research tools to identify the roles of different ADR subtypes and as therapeutic agents for multiple diseases related to dysfunction of the NA and adrenaline systems.

$\alpha$-adrenergic receptors further include three sub-types: $\alpha_{1A}$-adrenergic receptor ($\alpha_{1A}$-ADR), $\alpha_{1B}$-adrenergic receptor ($\alpha_{1B}$-ADR), and $\alpha_{1D}$-adrenergic receptor ($\alpha_{1D}$-ADR). Because these subtypes are expressed in distinct patterns and involved in different physiological processes, ligands that can selectively target one subtype have therapeutic potential for multiple diseases. However, discovery of subtype-selective ligands has been challenging due to a high level of sequence homology shared by these subtypes. A lot of existing agonists for $\alpha$-adrenergic receptors also exhibit inferior blood-brain-barrier (BBB) penetration. However, good drug BBB penetration is often required for an efficacious therapy for most central nervous system (CNS) indications.

As a class of G-protein coupled receptor, adrenergic receptors signal via G protein- and arrestin-dependent pathways. G protein- or arrestin signaling can mediate different physiological responses. Recently, it has become clear that agonists can show biased activation of signaling pathways. The ability of ligands to activate the receptor and produce responses in a pathway-dependent manner has been termed "signaling bias" or "functional selectivity". As G proteins and arrestins mediate distinct physiological processes, biased agonists can provide improved therapeutic selectivity with reduced adverse effects. Thus, the present disclosure is directed to adrenergic receptor subtype-selective agonists with improved blood-brain-barrier (BBB) penetration.

An adrenergic receptor modulating compound can be an agonist of the target adrenergic receptor. In some cases, an effective amount of an adrenergic receptor modulating compound is an amount sufficient to activate an activity related to the adrenergic receptor in a cell by 10% or more, such as 20% or more, 30% or more, 40% or more, 50% or more, 60% or more, 70% or more, 80% or more, 90% or more, 100% or more, 200% or even more relative to a control, e.g., a control cell exhibiting a known activity level of the receptor.

The adrenergic receptor modulating compound can be a partial agonist of the target adrenergic receptor. In some cases, an effective amount of an adrenergic receptor modulating compound is an amount sufficient to achieve partially agonism of the adrenergic receptor in a cell, e.g., where the subject compound achieves 10% activation or more of the receptor, such as 20% or more, 30% or more, 40% or more, 50% or more, 60% or more, 70% or more, 80% or more, or 90% or more, relative to a control, e.g., a receptor that is fully activated. Partial agonism may be assessed using any convenient methods, such as a cell based assay using a known full agonist as a 100% activation control, where the relative maximum activation of the receptor can be measured relative to the full agonist.

The adrenergic receptor modulating compound can be an antagonist of the target adrenergic receptor. In some cases, an effective amount of an adrenergic receptor modulating compound is an amount sufficient to inhibit or decrease the activity of the target adrenergic receptor in a sample by 10% or more, such as 20% or more, 30% or more, 40% or more, 50% or more, 60% or more, 70% or more, 80% or more, 90% or more, or even more relative to a control, e.g., a sample not contacted with the compound of interest.

In some embodiments of the method, the target adrenergic receptor is a $\alpha_{1A}$-adrenergic receptor.

The target adrenergic receptor may be one that is responsible for a mediating an intracellular signal or pathway in a cell. In some embodiments, the sample includes a cell and modulating the adrenergic receptor modulates a physiological process in the cell. Any convenient physiological processes can be targeted for modulation in a cell using the subject methods. In some embodiments, the physiological process is one that is implicated in cardiac function, in certain instances, the physiological process is one that is implicated in cognitive function. In certain instances, the physiological process is one that is implicated in an inflammatory pathway or condition. The subject methods can provide for mediation of the intracellular concentration of a signaling molecule in a cell, such as cAMP. The subject methods can provide for partial or full blockage of the target adrenergic receptor to result in modulation (e.g., activation) of cAMP in a sample. In some embodiments, the method does not modulate β-arrestin pathways of the cell. In some cases, the cells are inflammatory cells and the function of the cells is regulated. The subject methods can provide for inhibition of an inflammatory pathway in a cell. In some cases, TNF-alpha is inhibited in the cell, e.g., the concentration or production of TNF-alpha is reduced by practicing the subject method. In certain embodiments of the method, the cell is a neuron. In some embodiments, modulating the adrenergic receptor enhances neurogenesis.

The compounds of this disclosure may be employed in a conventional manner for controlling, preventing, treating a disease described herein, including, but not limited to, myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, neuronal ceroid lipofuscinosis, cerebral autosomal dominant arteriopathy with subcortical infarcts (CADASIL) and diabetic retinopathy. Such methods of treatment, their dosage levels and requirements may be selected by those of ordinary skill in the art from available methods and techniques.

Some aspects and embodiments of the instant disclosure are based, at least in part, on the finding that partial agonism of an $\alpha_{1A}$-AR receptor with a relatively low dose of an $\alpha_{1A}$-AR partial agonist can increase cardiac output, resulting from improved venous return and myocardial contractility, without a concomitant increase in arteriolar vascular resistance, thus resulting in an increase in blood flow to various parts of the body, including the brain. Therefore, compositions and methods are provided herein that include identifying a patient having a nOH, or a disease or disorder associated with low cerebral blood flow (CBF) and/or fluctuations in CBF, and administering to the patient an $\alpha_{1A}$-AR partial agonist.

In this regard, while not wishing to be bound to any one particular theory, $\alpha_{1A}$-AR receptors are preferentially found on the venous vascular branches and on the ventricular myocytes. Activation of $\alpha_{1A}$-AR receptors activates smooth muscles in the venous vascular branches, to lower venous capacitance and encourage blood return to feed the heart, and also activates the cardiomyocytes increasing pump action—a cardiotonic with a physiological inotropic effect. With increased venous return, preload is increased, thus raising the filling volume of heart; with the inotropic effect, the ejection function is enhanced, both combining to deliver more output to the arteries. However, unlike the indirect sympathomimetic droxidopa/Northera or the non-selective al-AR agonist midodrine, an $\alpha_{1A}$-AR partial agonist, in certain embodiments will spare the arteriolar smooth muscles (largely $\alpha_{1B}$-AR and $\alpha_{1D}$-AR function), and so peripheral vascular resistance is not significantly raised (no 'afterload' elevation). As such, BP rise will be less strong (especially in the supine position) and the increased cardiac output will readily perfuse the organs, including the brain.

Accordingly, the present disclosure includes methods and compositions for treating diseases, disorders, or conditions that are associated with, or caused by impairment (or relative decrease) in one or both of (a) cardiac output and (b) venous return.

In certain aspects and embodiments of the present disclosure compositions and methods result in an improved cognition, raised cerebral metabolic activity and/or improved inflammatory control in a patient. In some embodiments the methods described herein result in an improvement cognition, for example as demonstrated by an improvement in a cognition test or model; a memory test; a diagnostic indicator of mental status, brain function, mental condition; a contextual learning test; or the like in the patient. Such cognitive tests, diagnostics and models are well known in the art. In various aspects and embodiments, any of many accepted contextual learning tests for animals or humans can be used to assess baseline cognitive function and/or to measure or quantify improved cognitive function. In some embodiments, the compositions and methods described herein may result in an improvement one or more tests, diagnostics and models as follows. Likewise, for the raised cerebral metabolic activity and improved inflammatory control—these in certain embodiments may be imaged via FDG-PET and via sampling of cerebrospinal fluid (CSF) allowing measures of inflammatory cytokines and markers of glial cell activation.

Orthostatic hypotension (OH), also known as postural hypotension, is a form of low blood pressure which occurs when a person stands up. In medical terms, OH is defined as a fall in systolic blood pressure of at least 20 or 30 mm Hg or diastolic blood pressure of at least 10 mm Hg within three minutes of a postural change from supine to upright position (Neurology 1996; 46:1470). OH can produce a wide variety of symptoms including dizziness, lightheadedness and syncope (fainting), as well as discomfort in the upper chest and shoulder region ('coat hanger' pain). Due to these symptoms, OH often curtails or even prevents daily activities that require standing or walking. Additionally, OH is associated with increased morbidity and mortality. See, for example, Jones et al, Expert Review of Cardiovascular Therapy, 2015; 13:11, 1263-1276; Kuritzky et al., Postgrad. Med. 2015; 127(7):702-715; and Low et al, J. Clin. Neurol., 2015; 11(3):220-226.

The underlying causes of OH can be broadly divided into neurogenic and non-neurogenic categories. Neurogenic orthostatic hypotension (nOH) is a form of OH involving the nervous system, e.g., OH caused by a peripheral or central neurologic disorder, such as primary autonomic failure (including pure autonomic failure, multiple system atrophy, and Parkinson's disease), and autonomic neuropathy (dysautonomia) (including diabetic and nondiabetic autonomic neuropathy) (Arbique et al., JAMDA 15 (2014) 234-239). Such disorders can cause a deficiency or dysregulation of norepinephrine which is the primary neurotransmitter that regulates blood pressure in response to postural changes (Loavenbruck et al, Curr. Med. Res. Opin., 2015; 31:2095-2104). As a result, the autonomic nervous system fails to properly regulate blood pressure during a postural change and the patient experiences a significant fall in blood pressure resulting in, e.g., dizziness, lightheadedness, or syncope.

Accordingly, the management of the nOH condition requires, most fundamentally, increasing cerebral blood flow (CBF) in the context of an otherwise pathological fall in blood pressure, on supine to standing posture changes in patients. In various aspects and embodiments of the compositions and methods provided herein, an $\alpha_{1A}$-AR partial agonist is administered to a patient having nOH, and the actions of the partial agonist make less frequent and less severe associated signs and symptoms of nOH, including light-headedness/dizziness, pre-syncopal symptoms, syncope/blackout, and 'coat-hanger pain'. By maintaining better CBF, patients in some embodiments will also maintain improved cognitive function, especially those prone to 'fluctuations' which are commonly seen in the synucleinopathy conditions often typically associated with nOH. Symptoms/tests/screening for nOH an descriptions of some treatments can be found in Eschlbock et al, J Neural Tansm, (2017) 124:1567-1605 and Gibbons et al, J Neurol, (2017) 264:1567-1582.

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

In some embodiments, the subject method includes administering a therapeutically effective amount of one or more additional active agents. By combination therapy is meant that an adrenergic receptor modulating compound can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition.

The subject compounds can be administered in combination with other therapeutic agents in a variety of therapeutic applications. Therapeutic applications of interest for combination therapy include those applications in which activity of a target adrenergic receptor is the cause or a compounding factor in disease progression. As such, the subject compounds find use in combination therapies in which the inhibition of a target adrenergic receptor in the subject is desired. Examples of disease conditions which may be treated by a combination therapy including a subject compound include, but are not limited to, cardiac conditions or diseases, neurodegenerative or neurodevelopmental disease, respiratory disorders, asthma, memory impairment, depression, inflammatory diseases, stroke, ischemic brain or tissue injury and cancer. Agents of interest which can be used in jointly with the subject adrenergic receptor modulating compounds include, but are not limited to, antidepressants, antipsychotics, beta-blockers, vasoconstrictors, antihypotensives, decongestants, chemotherapeutic agents, agents used in Alzheimer's disease, and anti-inflammatory agents.

The subject adrenergic receptor modulating compounds can be used jointly with any agent useful in the treatment of a cardiac condition, such as cardiogenic shock, hypertension, congestive heart failure, coronary heart disease, arrhythmias, myocardial infarction or ischemic heart diseases. Agents of interest which can be used in jointly with the subject adrenergic receptor modulating compounds include, but are not limited to, denopamine, dobutamine, xamoterol, acebutolol, atenolol, betaxolol, bisoprolol, pindolol, esmolol, metoprolol, nebivolol, vortioxetine, Carvedilol, Labetalol, Phentolamine, Prazosin, Cirazoline, Methoxamine, Synephrine, Etilefrine, Metaraminol, Midodrine, and cumarin.

The subject adrenergic receptor modulating compounds can be used jointly with any agent useful in the treatment of a neurodegenerative or neurodevelopmental disease, such as such as Alzheimer's Disease, memory impairment, cognitive impairment, depression, stroke and ischemic brain or tissue injury, Down's syndrome or Autism. Agents of interest which can be used in jointly with the subject adrenergic receptor modulating compounds include, but are not limited to, acepromazine. In some embodiments, the subject adrenergic receptor modulating compounds can be used in the treatment of a disease, such as a neurodegenerative or neurodevelopmental disease, in combination with a cholinesterase inhibitor or a NMDA receptor modulators. Agents of interest include, but are not limited to, Donepezil, Aricept, Galantamine, Razadyne, Memantine, Namenda, Rivastigmine, Exelon, Tacrine and Cognex. Other agents of interest which can be used in jointly with the subject adrenergic receptor modulating compounds include, but are not limited to, 4-NEMD, 7-Me-marsanidine, Agmatine, Apraclonidine, Brimonidine, Cannabigerol, Clonidine, Detomidine, Dexmedetomidine, Fadolmidine, Guanabenz, Guanfacine, Lofexidine, Marsanidine, Medetomidine, Methamphetamine, Mivazerol, Rilmenidine, Romifidine, Talipexole, Tiamenidine, Tizanidine, Tolonidine, Xylazine, Xylometazoline, Aripiprazole, Asenapine, Atipamezole, Cirazoline, Clozapine, Efaroxan, Idazoxan, Lurasidone, Melperone, Mianserin, Mirtazapine, Napitane, Olanzapine, Paliperidone, Phenoxybenzamine, Phentolamine, Piribedil, Rauwolscine, Risperidone, Rotigotine, Quetiapine, Norquetiapine, Setiptiline, Tolazoline, Yohimbine, Ziprasidone and Zotepine. Other agents of interest which can be used in jointly with the subject adrenergic receptor modulating compounds include, but are not limited to, bitolterol, fenoterol, hexoprenaline, isoprenaline or isoproterenol, levosalbutamol or levalbuterol, orciprenaline or metaproterenol, pirbuterol, procaterol, salbutamol or albuterol, terbutaline, bambuterol, clenbuterol, formoterol, salmeterol, carmoterol, indacaterol, milveterol, olodaterol, vilanterol, fenoterol, hexoprenaline, isoxsuprine, ritodrine, salbutamol or albuterol, terbutaline, zilpaterol, ICI-118,551 and butoxamine.

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to stroke, ischemia, Alzheimer's, ankylosing spondylitis, arthritis, osteoarthritis, rheumatoid arthritis, psoriatic arthritis, asthma atherosclerosis, Crohn's disease, colitis, dermatitis diverticulitis, fibromyalgia, hepatitis, irritable bowel syndrome, systemic lupus erythematous, nephritis, ulcerative colitis and Parkinson's disease. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topically-administered transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

Also provided are kits that include the disclosed adrenergic receptor modulating compounds. Systems of the present disclosure include collections of active agents brought together, e.g., by a health care practitioner, for administration to a subject, such as a patient. Such systems may include an adrenergic receptor modulating compound and one or more additional active agents disclosed herein. Kits that include adrenergic receptor modulating compounds which are provided that may include one or more dosages of an adrenergic receptor modulating compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the as disclosed herein, e.g., instructions for using the subject unit doses to treat cellular proliferative disease conditions. These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are provided to further illustrate the advantages and features of the present disclosure, but they are not intended to limit the scope of the disclosure. While the examples are typical of those that might be used, other procedures, methodologies, or techniques known to those skilled in the art may alternatively be used. Table 1 below illustrates exemplary compounds synthesized of the present disclosure.

TABLE 1

| Exemplary Compounds | | |
|---|---|---|
| Compound | Structure | [M + H] |
| 1 | 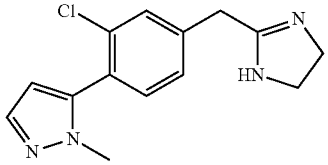 [SMILES: Cn1nccc1-c1ccc(CC2=NCCN2)cc1Cl] | 275.1 |
| 2 | 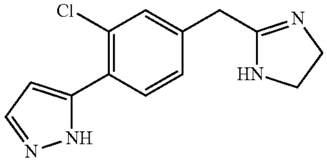 [SMILES: Clc1cc(CC2=NCCN2)ccc1-c1ccn[nH]1] | 261.1 |
| 3 | 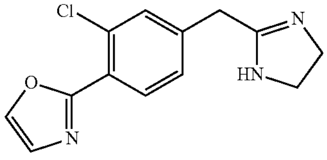 [SMILES: Clc1cc(CC2=NCCN2)ccc1-c1ncco1] | 262.0 |
| 4 | 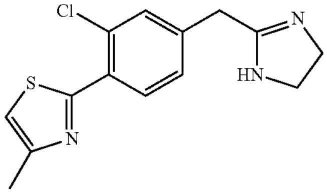 [SMILES: Cc1csc(-c2ccc(CC3=NCCN3)cc2Cl)n1] | 292.0 |
| 5 | 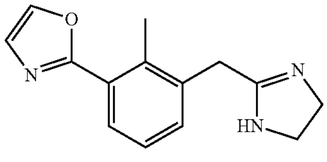 [SMILES: Cc1c(CC2=NCCN2)cccc1-c1ncco1] | 242.1 |
| 6 | 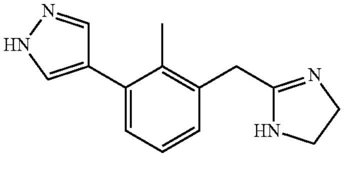 [SMILES: Cc1c(CC2=NCCN2)cccc1-c1cn[nH]c1] | 241.1 |
| 7 | 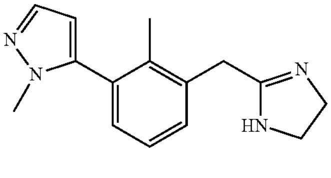 [SMILES: Cc1c(CC2=NCCN2)cccc1-c1ccnn1C] | 255.1 |
| 8 | 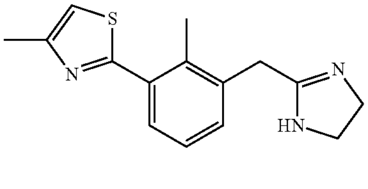 [SMILES: Cc1csc(-c2cccc(CC3=NCCN3)c2C)n1] | 272.1 |
| 9 | 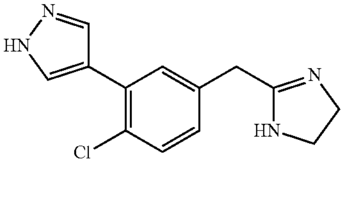 [SMILES: Clc1ccc(CC2=NCCN2)cc1-c1cn[nH]c1] | 267.2 |

TABLE 1-continued

TABLE 1-continued
| Exemplary Compounds | | |
|---|---|---|
| Compound | Structure | [M + H] |
| 10 | 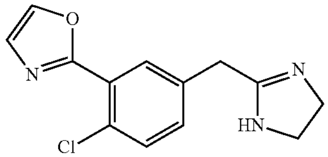 [SMILES: Clc1ccc(CC2=NCCN2)cc1-c1ncco1] | 262.0 |
| 11 | 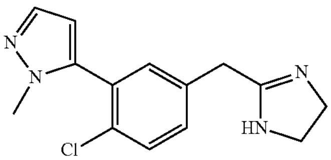 [SMILES: Cn1nccc1-c1cc(CC2=NCCN2)ccc1Cl] | 275.1 |
| 12 | 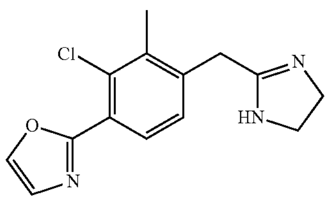 [SMILES: Cc1c(CC2=NCCN2)ccc(-c2ncco2)c1Cl] | 276.1 |
| 13 | 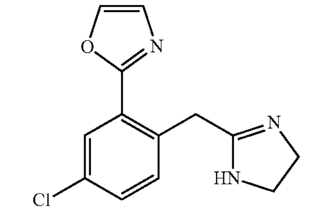 [SMILES: Clc1ccc(CC2=NCCN2)c(-c2ncco2)c1] | 262.1 |
| 14 | 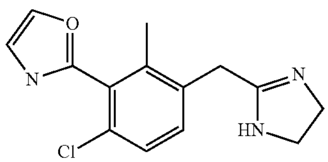 | 276.1 |
| 15 | 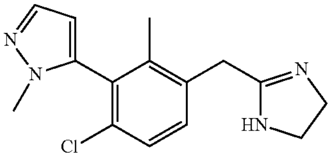 [SMILES: Cc1c(CC2=NCCN2)ccc(Cl)c1-c1ccnn1C] | 289.1 |
| 16 | 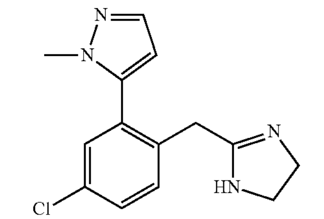 [SMILES: Cn1nccc1-c1cc(Cl)ccc1CC1=NCCN1] | 275.1 |
TABLE 1-continued
| Exemplary Compounds | | |
|---|---|---|
| Compound | Structure | [M + H] |
| 17 | 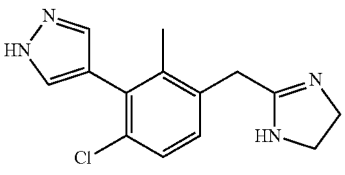 [SMILES: Cc1c(CC2=NCCN2)ccc(Cl)c1-c1cn[nH]c1] | 275.1 |
| 18 | 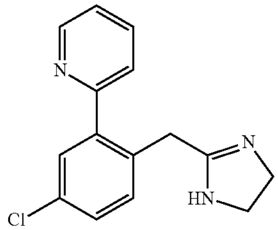 [SMILES: Clc1ccc(CC2=NCCN2)c(-c2ccccn2)c1] | 272.1 |
| 19 | 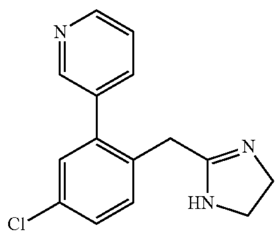 [SMILES: Clc1ccc(CC2=NCCN2)c(-c2cccnc2)c1] | 272.1 |
| 20 | 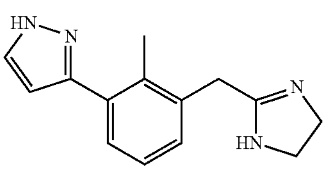 [SMILES: Cc1c(CC2=NCCN2)cccc1-c1cc[nH]n1] | 241.1 |
| 21 | 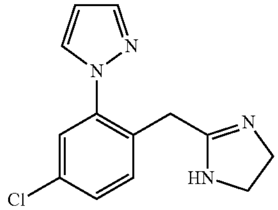 [SMILES: Clc1ccc(CC2=NCCN2)c(-n2cccn2)c1] | 261.1 |
| 22 | 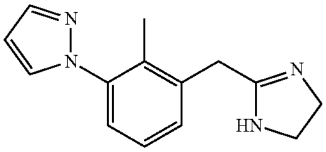 [SMILES: Cc1c(CC2=NCCN2)cccc1-n1cccn1] | 241.1 |
| 23 | 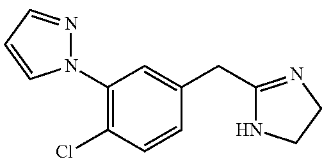 [SMILES: Clc1ccc(CC2=NCCN2)cc1-n1cccn1] | 261 |

TABLE 1-continued
| Compound | Structure | [M + H] |
| --- | --- | --- |
| 24 | 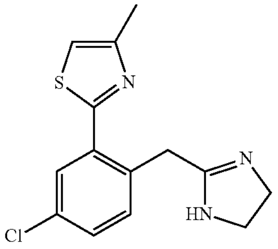 [SMILES: Cc1csc(-c2cc(Cl)ccc2CC2=NCCN2)n1] | 292 |
| 25 | 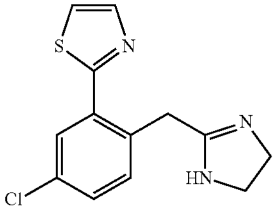 [SMILES: Clc1ccc(CC2=NCCN2)c(-c2nccs2)c1] | 278 |
| 26 | 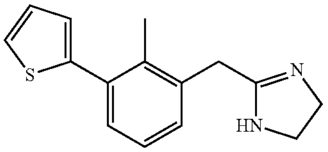 [SMILES: Cc1c(CC2=NCCN2)cccc1-c1cccs1] | 257 |
| 27 | 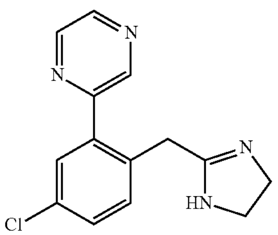 [SMILES: Clc1ccc(CC2=NCCN2)c(-c2cnccn2)c1] | 273 |
| 28 | 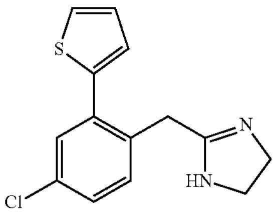 [SMILES: Clc1ccc(CC2=NCCN2)c(-c2cccs2)c1] | 277 |
| 29 | 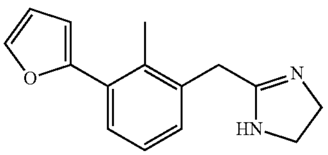 [SMILES: Cc1c(CC2=NCCN2)cccc1-c1ccco1] | 241.1 |
| 30 | 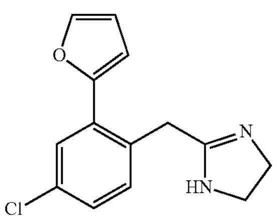 [SMILES: Clc1ccc(CC2=NCCN2)c(-c2ccco2)c1] | 261 |
TABLE 1-continued
| Compound | Structure | [M + H] |
| --- | --- | --- |
| 31 | 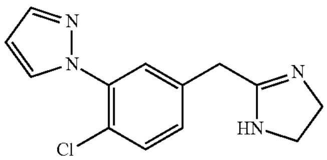 [SMILES: Clc1ccc(CC2=NCCN2)cc1-n1cccn1] | 275 |
| 32 | 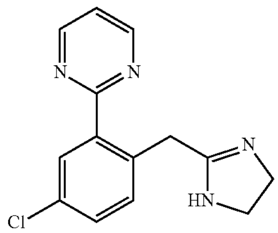 [SMILES: Clc1ccc(CC2=NCCN2)c(-c2ncccn2)c1] | 273 |
| 33 | 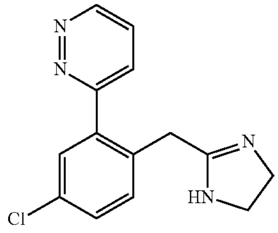 [SMILES: Clc1ccc(CC2=NCCN2)c(-c2cccnn2)c1] | 273 |
| 34 | 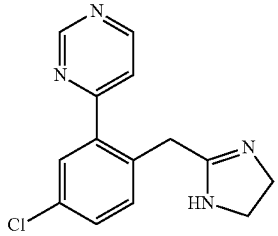 [SMILES: Clc1ccc(CC2=NCCN2)c(-c2ccncn2)c1] | 273 |
| 35 | 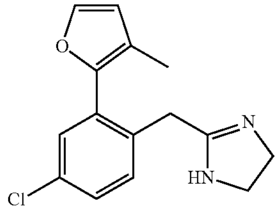 [SMILES: Cc1ccoc1-c1cc(Cl)ccc1CC1=NCCN1] | 275.0 |
| 36 | 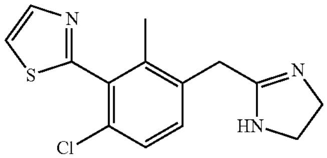 [SMILES: Cc1c(CC2=NCCN2)ccc(Cl)c1-c1nccs1] | 291.9 |

TABLE 1-continued
| Exemplary Compounds | | |
|---|---|---|
| Compound | Structure | [M + H] |
| 37 | 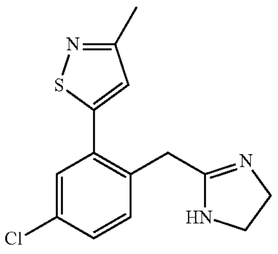 [SMILES: Cc1cc(-c2cc(Cl)ccc2CC2=NCCN2)sn1] | 292 |
| 38 | 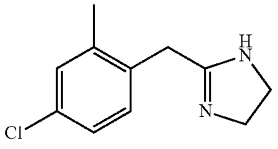 | 209 |
| 39 | 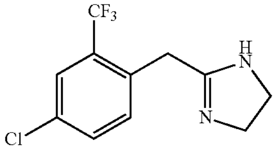 [SMILES: FC(F)(F)c1cc(Cl)ccc1CC1=NCCN1] | 263 |
| 40 | 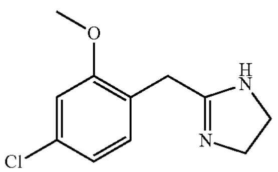 | 225.0 |
| 41 | 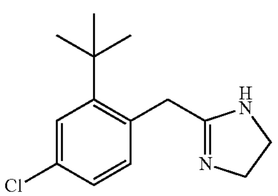 [SMILES: CC(C)(C)c1cc(Cl)ccc1CC1=NCCN1] | 251.1 |
| 42 | 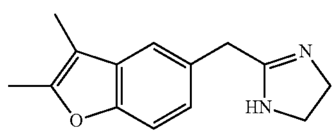 [SMILES: Cc1oc2ccc(CC3=NCCN3)cc2c1C] | 229.1 |
| 43 | 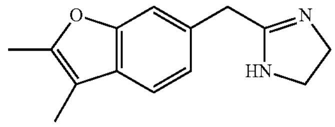 [SMILES: Cc1oc2cc(CC3=NCCN3)ccc2c1C] | 229.1 |
| 44 | 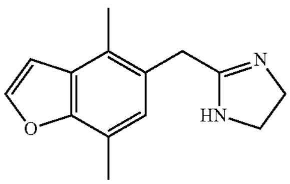 [SMILES: Cc1c(CC2=NCCN2)cc(C)c2occc12] | 229.1 |
TABLE 1-continued
| Exemplary Compounds | | |
|---|---|---|
| Compound | Structure | [M + H] |
| 45 | 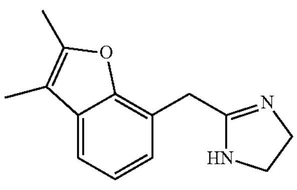 [SMILES: Cc1oc2c(CC3=NCCN3)cccc2c1C] | 229.1 |
| 46 | 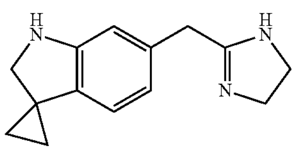 [SMILES: c1cc2c(cc1CC1=NCCN1)NCC21CC1] | 228.1 |
| 47 | 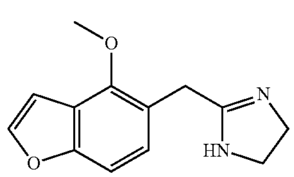 [SMILES: COc1c(CC2=NCCN2)ccc2occc12] | 231.1 |
| 48 | 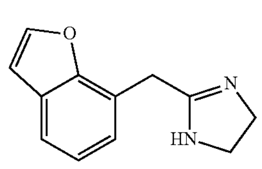 [SMILES: c1cc(CC2=NCCN2)c2occc2c1] | 201.0 |
| 49 | 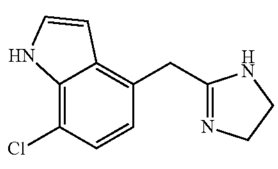 [SMILES: Clc1ccc(CC2=NCCN2)c2cc[nH]c12] | 201.1 |
| 50 | 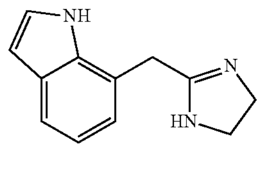 [SMILES: c1cc(CC2=NCCN2)c2[nH]ccc2c1] | 200.1 |
| 51 | 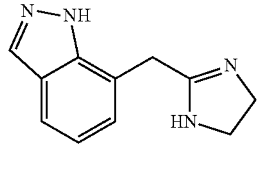 [SMILES: c1cc(CC2=NCCN2)c2[nH]ncc2c1] | 201.1 |
| 52 | 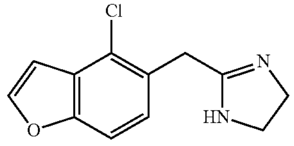 [SMILES: Clc1c(CC2=NCCN2)ccc2occc12] | 235.0 |

TABLE 1-continued
| Exemplary Compounds | | |
|---|---|---|
| Compound | Structure | [M + H] |
| 53 | 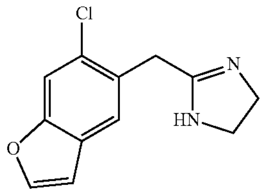 [SMILES: Clc1cc2occc2cc1CC1=NCCN1] | 235.0 |
| 54 | 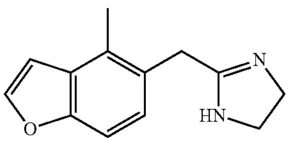 [SMILES: Cc1c(CC2=NCCN2)ccc2occc12] | 215.1 |
| 55 | 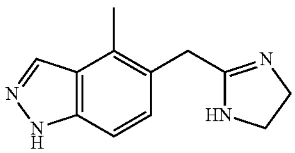 [SMILES: Cc1c(CC2=NCCN2)ccc2[nH]ncc12] | 215.1 |
| 56 | 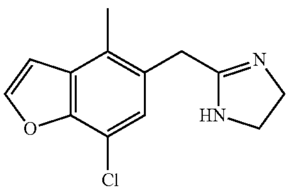 [SMILES: Cc1c(CC2=NCCN2)cc(Cl)c2occc12] | 249.0 |
| 57 | 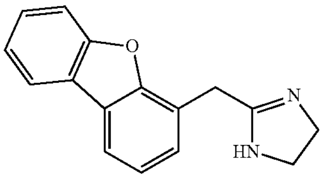 [SMILES: c1ccc2c(c1)oc1c(CC3=NCCN3)cccc12] | 217.1 |
| 58 | 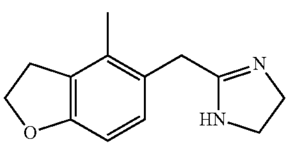 [SMILES: Cc1c(CC2=NCCN2)ccc2c1CCO2] | 217.1 |
| 59 | 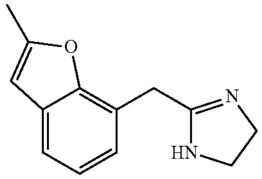 [SMILES: Cc1cc2cccc(CC3=NCCN3)c2o1] | 215.1 |
| 60 | 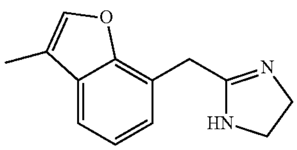 [SMILES: Cc1coc2c(CC3=NCCN3)cccc12] | 215.1 |
TABLE 1-continued
| Exemplary Compounds | | |
|---|---|---|
| Compound | Structure | [M + H] |
| 61 | 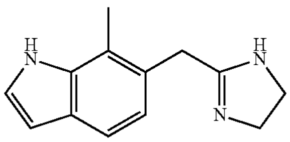 [SMILES: Cc1c(CC2=NCCN2)ccc2cc[nH]c12] | 214.1 |
| 62 | 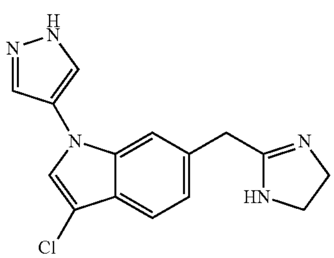 [SMILES: Clc1cn(-c2cn[nH]c2)c2cc(CC3=NCCN3)ccc12] | 300.1 |
| 63 | 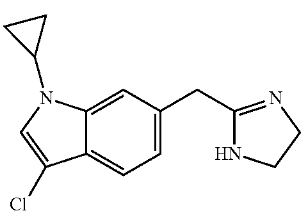 [SMILES: Clc1cn(C2CC2)c2cc(CC3=NCCN3)ccc12] | 274.1 |
| 64 | 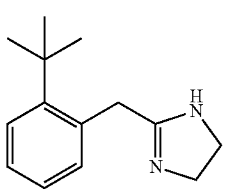 [SMILES: CC(C)(C)c1ccccc1CC1=NCCN1] | 217.1 |
| 65 | 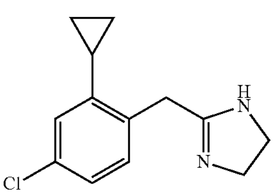 [SMILES: Clc1ccc(CC2=NCCN2)c(C2CC2)c1] | 235.1 |
| 66 | 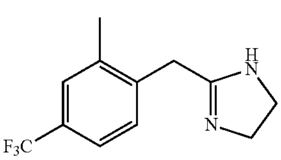 | 243.1 |
| 67 | 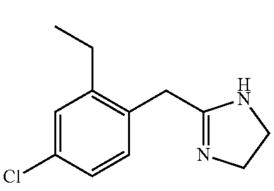 | 223.1 |

TABLE 1-continued
| Exemplary Compounds | | |
|---|---|---|
| Compound | Structure | [M + H] |
| 68 | 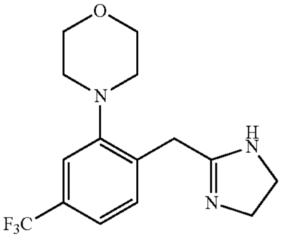 [SMILES: FC(F)(F)c1ccc(CC2=NCCN2)c(N2CCOCC2)c1] | 314.0 |
| 69 | 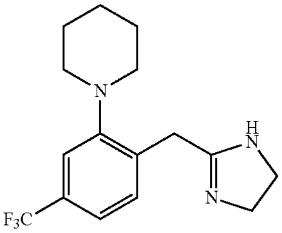 | 312.0 |
| 70 | 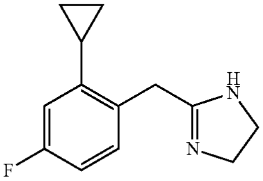 [SMILES: Fc1ccc(CC2=NCCN2)c(C2CC2)c1] | 219.2 |
| 71 | 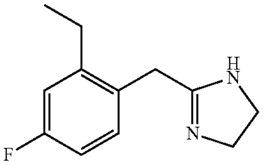 | 207.3 |
| 72 | 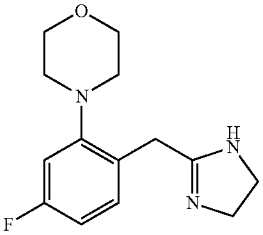 [SMILES: Fc1ccc(CC2=NCCN2)c(N2CCOCC2)c1] | 264.2 |
| 73 | 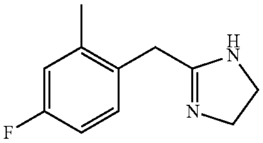 | 193.2 |
TABLE 1-continued
| Exemplary Compounds | | |
|---|---|---|
| Compound | Structure | [M + H] |
| 74 | 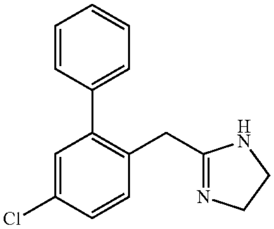 [SMILES: Clc1ccc(CC2=NCCN2)c(-c2ccccc2)c1] | 271.1 |
| 75 | 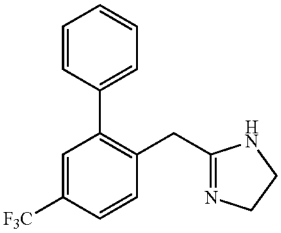 [SMILES: FC(F)(F)c1ccc(CC2=NCCN2)c(-c2ccccc2)c1] | 305.0 |
| 76 | 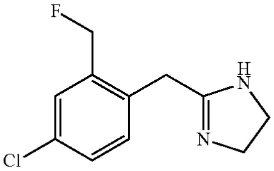 [SMILES: FCc1cc(Cl)ccc1CC1=NCCN1] | 227.0 |
| 77 | 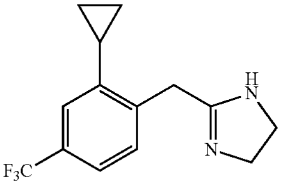 [SMILES: FC(F)(F)c1ccc(CC2=NCCN2)c(C2CC2)c1] | 269.0 |
| 78 | 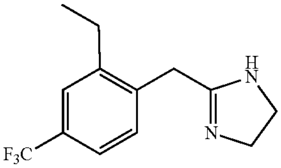 [SMILES: CCc1cc(C(F)(F)F)ccc1CC1=NCCN1] | 257.1 |
| 79 | 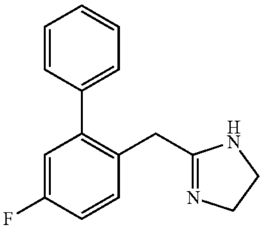 [SMILES: Fc1ccc(CC2=NCCN2)c(-c2ccccc2)c1] | 255.1 |
| 80 | 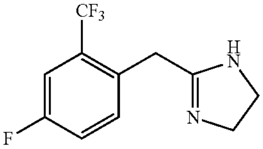 [SMILES: Fc1ccc(CC2=NCCN2)c(C(F)(F)F)c1] | 247.0 |

TABLE 1-continued
| Exemplary Compounds | | |
|---|---|---|
| Compound | Structure | [M + H] |
| 81 | 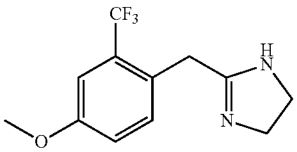 [SMILES: COc1ccc(CC2=NCCN2)c(C(F)(F)F)c1] | 259.0 |
| 82 | 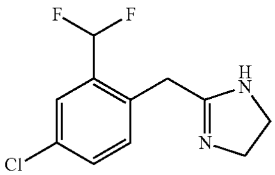 [SMILES: FC(F)c1cc(Cl)ccc1CC1=NCCN1] | 245.0 |
| 83 | 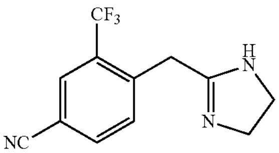 [SMILES: N#Cc1ccc(CC2=NCCN2)c(C(F)(F)F)c1] | 254.0 |
| 84 | 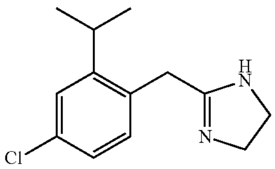 [SMILES: CC(C)c1cc(Cl)ccc1CC1=NCCN1] | 237.1 |
| 85 | 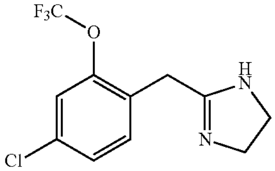 [SMILES: FC(F)(F)Oc1cc(Cl)ccc1CC1=NCCN1] | 279.0 |
| 86 | 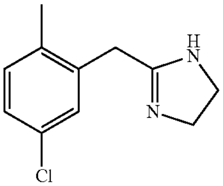 | 209.1 |
| 87 | 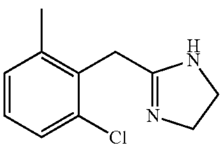 | 209.1 |
| 88 | 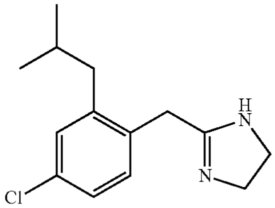 [SMILES: CC(C)Cc1cc(Cl)ccc1CC1=NCCN1] | 251.1 |
TABLE 1-continued
| Exemplary Compounds | | |
|---|---|---|
| Compound | Structure | [M + H] |
| 89 | 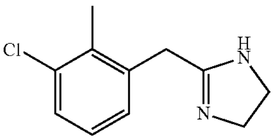 | 209.0 |
| 90 | 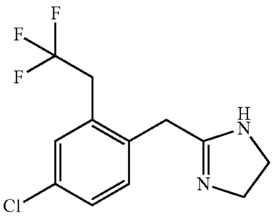 [SMILES: FC(F)(F)Cc1cc(Cl)ccc1CC1=NCCN1] | 277.0 |
| 91 | 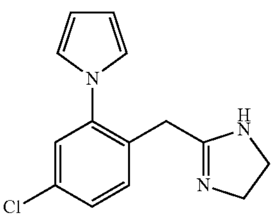 [SMILES: Clc1ccc(CC2=NCCN2)c(-n2cccc2)c1] | 260.0 |
| 92 | 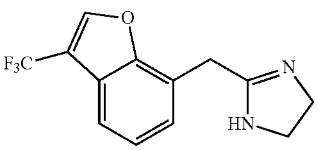 [SMILES: FC(F)(F)c1coc2c(CC3=NCCN3)cccc12] | 269.0 |
| 93 | 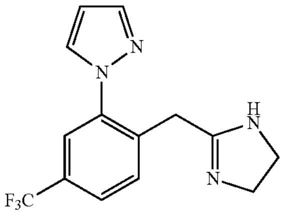 [SMILES: FC(F)(F)c1ccc(CC2=NCCN2)c(-n2cccn2)c1] | 295.0 |
| 94 | 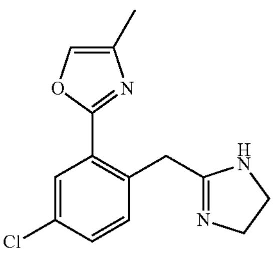 [SMILES: Cc1coc(-c2cc(Cl)ccc2CC2=NCCN2)n1] | 276.0 |
| 95 | 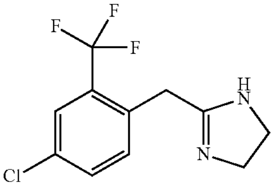 [SMILES: FC(F)(F)c1cc(Cl)ccc1CC1=NCCN1] | 259.0 |

TABLE 1-continued
| Exemplary Compounds | | |
|---|---|---|
| Compound | Structure | [M + H] |
| 96 | 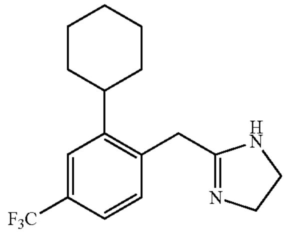 [SMILES: FC(F)(F)c1ccc(CC2=NCCN2)c(C2CCCCC2)c1] | 311.0 |
| 97 | 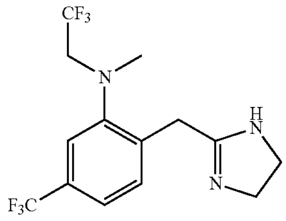 [SMILES: CN(CC(F)(F)F)c1cc(C(F)(F)F)ccc1CC1=NCCN1] | 340.0 |
| 98 | 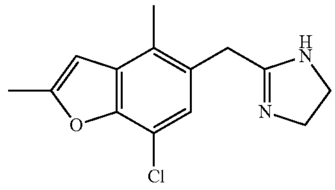 [SMILES: Cc1cc2c(C)c(CC3=NCCN3)cc(Cl)c2o1] | 263.0 |
| 99 | 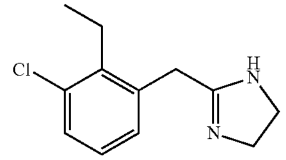 | 223.15 |
| 100 | 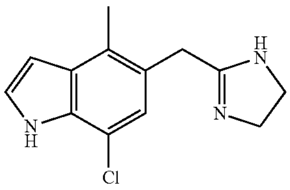 [SMILES: Cc1c(CC2=NCCN2)cc(Cl)c2[nH]ccc12] | 248.0 |
| 101 | 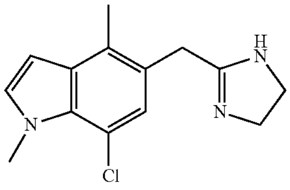 [SMILES: Cc1c(CC2=NCCN2)cc(Cl)c2c1ccn2C] | 262.1 |
| 102 | 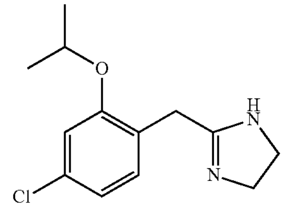 [SMILES: CC(C)Oc1cc(Cl)ccc1CC1=NCCN1] | 253.0 |
| 103 | 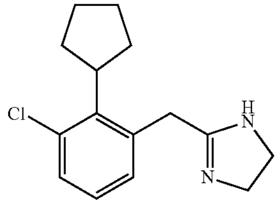 [SMILES: Clc1cccc(CC2=NCCN2)c1C1CCCC1] | 264.1 |
| 104 | 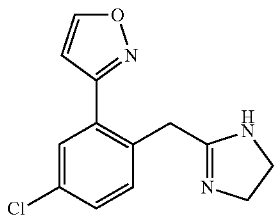 [SMILES: Clc1ccc(CC2=NCCN2)c(-c2ccon2)c1] | 262.0 |
| 105 | 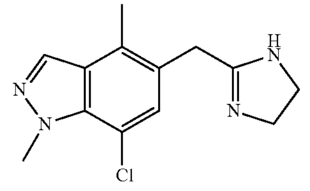 [SMILES: Cc1c(CC2=NCCN2)cc(Cl)c2c1cnn2C] | 263.0 |
| 106 | 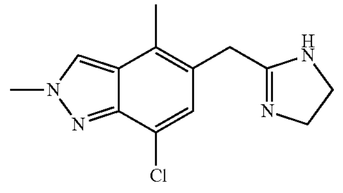 [SMILES: Cc1c(CC2=NCCN2)cc(Cl)c2nn(C)cc12] | 263.0 |
| 107 | 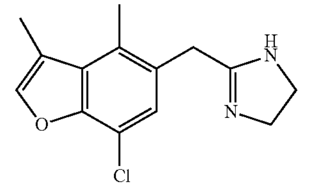 [SMILES: Cc1coc2c(Cl)cc(CC3=NCCN3)c(C)c12] | 263.0 |
| 108 | 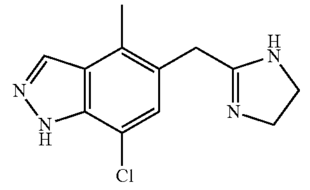 [SMILES: Cc1c(CC2=NCCN2)cc(Cl)c2[nH]ncc12] | 249.0 |
| 109 | 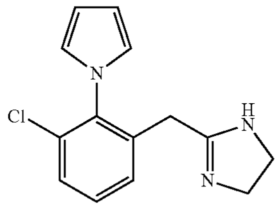 [SMILES: Clc1cccc(CC2=NCCN2)c1-n1cccc1] | 260.0 |

TABLE 1-continued
| Exemplary Compounds | | |
|---|---|---|
| Compound | Structure | [M + H] |
| 110 | 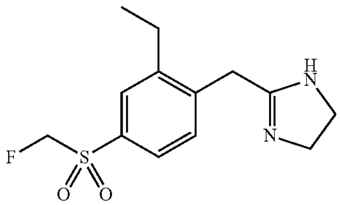 [SMILES: CCc1cc(S(=O)(=O)CF)ccc1CC1=NCCN1] | 285.0 |
| 111 | 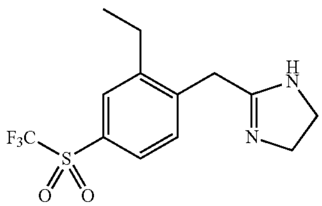 [SMILES: CCc1cc(S(=O)(=O)C(F)(F)F)ccc1CC1=NCCN1] | 321.1 |
| 112 | 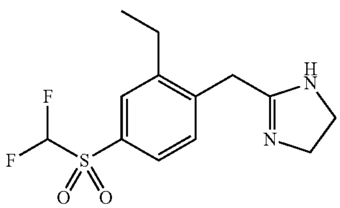 [SMILES: CCc1cc(S(=O)(=O)C(F)F)ccc1CC1=NCCN1] | 303.0 |
| 113 | 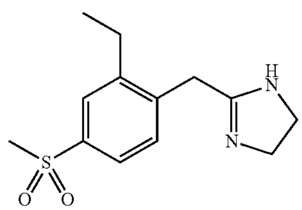 [SMILES: CCc1cc(S(C)(=O)=O)ccc1CC1=NCCN1] | 267.1 |
| 114 | 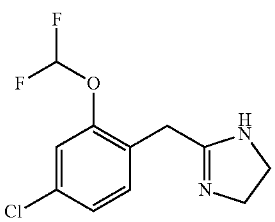 [SMILES: FC(F)Oc1cc(Cl)ccc1CC1=NCCN1] | 261.0 |
| 115 | 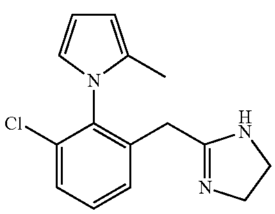 [SMILES: Cc1cccn1-c1c(Cl)cccc1CC1=NCCN1] | 274.1 |
TABLE 1-continued
| Exemplary Compounds | | |
|---|---|---|
| Compound | Structure | [M + H] |
| 116 | 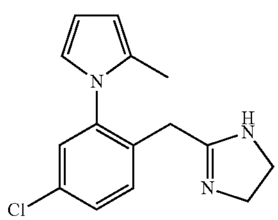 [SMILES: Cc1cccn1-c1cc(Cl)ccc1CC1=NCCN1] | 274.0 |
| 117 | 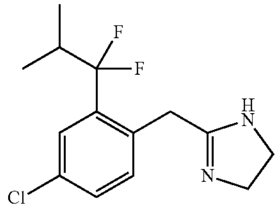 [SMILES: CC(C)C(F)(F)c1cc(Cl)ccc1CC1=NCCN1] | 287.0 |
| 118 | 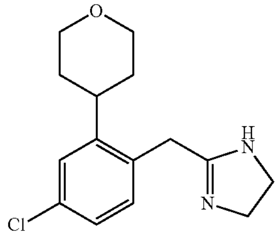 [SMILES: Clc1ccc(CC2=NCCN2)c(C2CCOCC2)c1] | 279.1 |
| 119 | 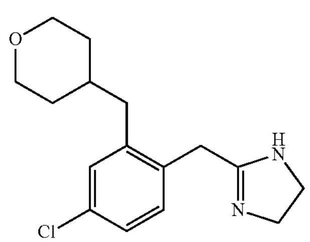 [SMILES: Clc1ccc(CC2=NCCN2)c(CC2CCOCC2)c1] | 293.1 |
| 120 | 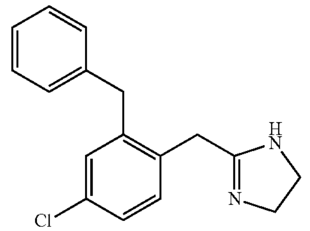 [SMILES: Clc1ccc(CC2=NCCN2)c(Cc2ccccc2)c1] | 285.0 |
| 121 | 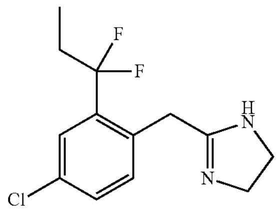 [SMILES: CCC(F)(F)c1cc(Cl)ccc1CC1=NCCN1] | 273.0 |

TABLE 1-continued
| Exemplary Compounds | | |
|---|---|---|
| Compound | Structure | [M + H] |
| 122 | 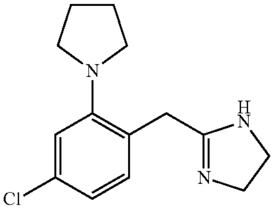 [SMILES: Clc1ccc(CC2=NCCN2)c(N2CCCC2)c1] | 264.1 |
| 123 | 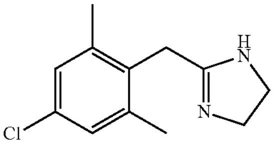 | 223.0 |
| 124 | 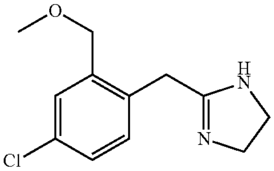 [SMILES: COCc1cc(Cl)ccc1CC1=NCCN1] | 239.0 |
| 125 | 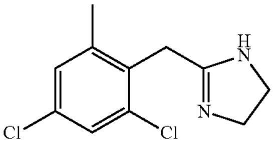 | 242.9 |
| 126 | 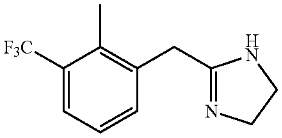 [SMILES: Cc1c(CC2=NCCN2)cccc1C(F)(F)F] | 243.3 |
| 127 | 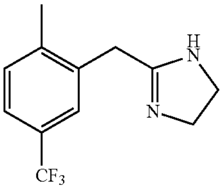 [SMILES: Cc1ccc(C(F)(F)F)cc1CC1=NCCN1] | 243.0 |
| 128 | 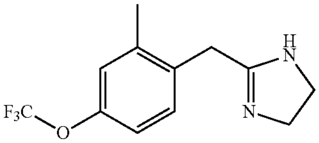 [SMILES: Cc1cc(OC(F)(F)F)ccc1CC1=NCCN1] | 259.0 |
| 129 | 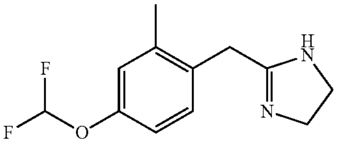 [SMILES: Cc1cc(OC(F)F)ccc1CC1=NCCN1] | 241.1 |
| 130 | 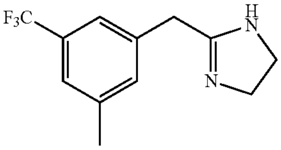 [SMILES: Cc1cc(CC2=NCCN2)cc(C(F)(F)F)c1] | 243.1 |
| 131 | 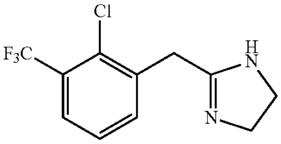 [SMILES: FC(F)(F)c1cccc(CC2=NCCN2)c1Cl] | 263.0 |
| 132 | 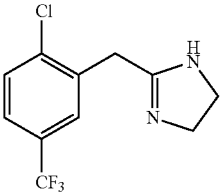 [SMILES: FC(F)(F)c1ccc(Cl)c(CC2=NCCN2)c1] | 263.0 |
| 133 | 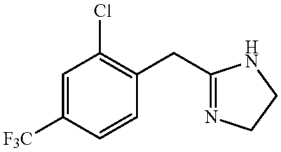 [SMILES: FC(F)(F)c1ccc(CC2=NCCN2)c(Cl)c1] | 263.0 |
| 134 | 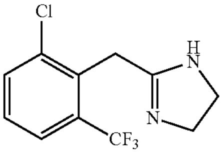 [SMILES: FC(F)(F)c1cccc(Cl)c1CC1=NCCN1] | 263.0 |
| 135 | 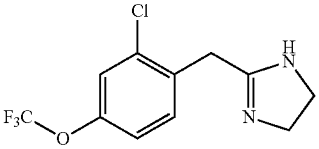 [SMILES: FC(F)(F)Oc1ccc(CC2=NCCN2)c(Cl)c1] | 279.0 |
| 136 | 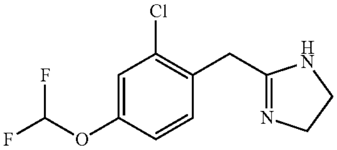 [SMILES: FC(F)Oc1ccc(CC2=NCCN2)c(Cl)c1] | 261.0 |
| 137 | 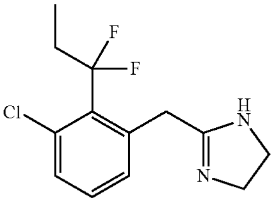 [SMILES: CCC(F)(F)c1c(Cl)cccc1CC1=NCCN1] | 273.0 |

TABLE 1-continued
| Exemplary Compounds | | |
|---|---|---|
| Compound | Structure | [M + H] |
| 138 | 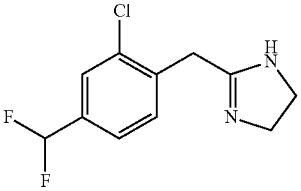 [SMILES: FC(F)c1ccc(CC2=NCCN2)c(Cl)c1] | 245.0 |
| 139 | 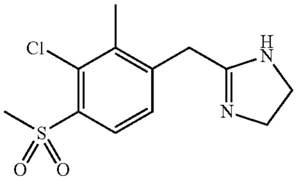 [SMILES: Cc1c(CC2=NCCN2)ccc(S(C)(=O)=O)c1Cl] | 287.0 |
| 140 | 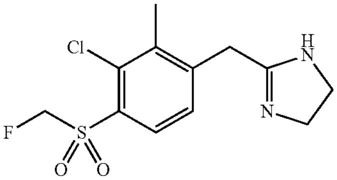 [SMILES: Cc1c(CC2=NCCN2)ccc(S(=O)(=O)CF)c1Cl] | 305.0 |
| 141 | 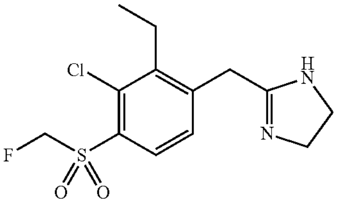 [SMILES: CCc1c(CC2=NCCN2)ccc(S(=O)(=O)CF)c1Cl] | 319.0 |
| 142 | 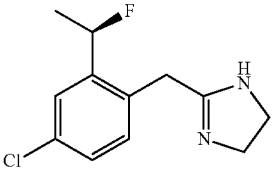 [SMILES: C[C@@H](F)c1cc(Cl)ccc1CC1=NCCN1] | 241.0 |
| 143 | 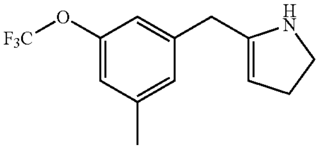 [SMILES: Cc1cc(CC2=CCCN2)cc(OC(F)(F)F)c1] | 259.0 |
| 144 | 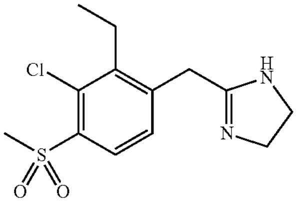 [SMILES: CCc1c(CC2=NCCN2)ccc(S(C)(=O)=O)c1Cl] | 301.0 |
TABLE 1-continued
| Exemplary Compounds | | |
|---|---|---|
| Compound | Structure | [M + H] |
| 145 | 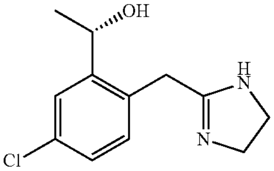 [SMILES: C[C@H](O)c1cc(Cl)ccc1CC1=NCCN1] | 239.0 |
| 146 | 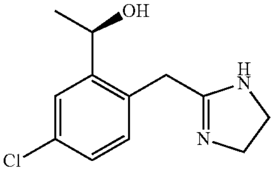 [SMILES: C[C@@H](O)c1cc(Cl)ccc1CC1=NCCN1] | 239.0 |
| 147 | 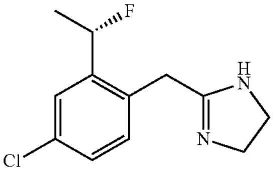 [SMILES: C[C@H](F)c1cc(Cl)ccc1CC1=NCCN1] | 241.0 |
| 148 | 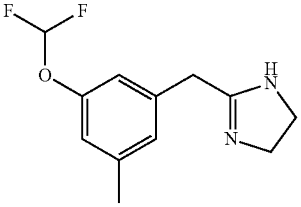 [SMILES: Cc1cc(CC2=NCCN2)cc(OC(F)F)c1] | 241.1 |
| 149 | 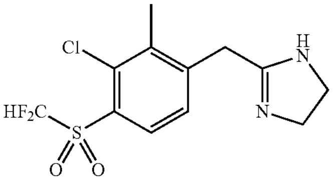 | 322.9 |
| 150 | 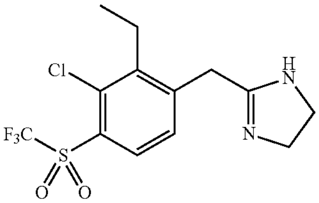 [SMILES: CCc1c(CC2=NCCN2)ccc(S(=O)(=O)C(F)(F)F)c1Cl] | 354.9 |
| 151 | 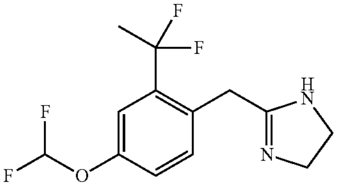 [SMILES: CC(F)(F)c1cc(OC(F)F)ccc1CC1=NCCN1] | 291.0 |

TABLE 1-continued
| Exemplary Compounds | | |
|---|---|---|
| Compound | Structure | [M + H] |
| 152 | 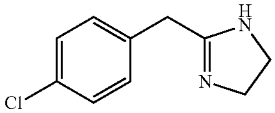 [SMILES: Clc1ccc(CC2=NCCN2)cc1] | 195 |
| 153 | 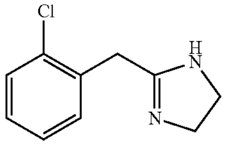 [SMILES: Clc1ccccc1CC1=NCCN1] | 195 |
| 154 | 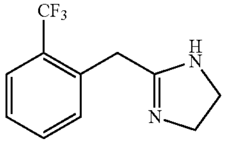 [SMILES: FC(F)(F)c1ccccc1CC1=NCCN1] | 229 |
| 155 | 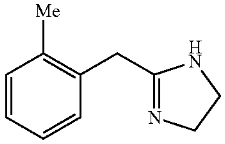 [SMILES: Cc1ccccc1CC1=NCCN1] | 175.1 |
| 156 | 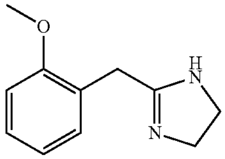 | 191.1 |
| 157 | 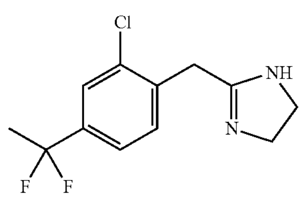 [SMILES: CC(F)(F)c1ccc(CC2=NCCN2)c(Cl)c1] | 259.0 |
| 158 | 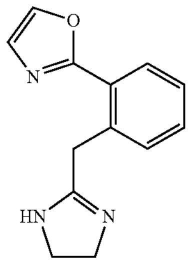 [SMILES: c1ccc(-c2ncco2)c(CC2=NCCN2)c1] | 228.1 |
| 159 | 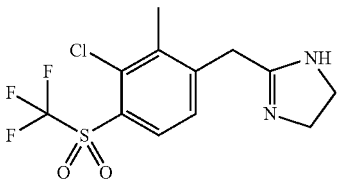 [SMILES: Cc1c(CC2=NCCN2)ccc(S(=O)(=O)C(F)(F)F)c1Cl] | 340.0 |
TABLE 1-continued
| Exemplary Compounds | | |
|---|---|---|
| Compound | Structure | [M + H] |
| 160 | 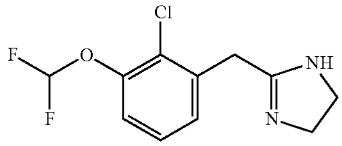 [SMILES: FC(F)Oc1cccc(CC2=NCCN2)c1Cl] | 261.0 |
| 161 | 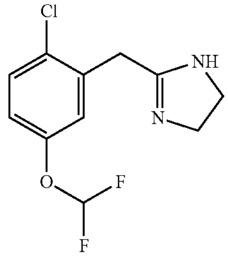 [SMILES: FC(F)Oc1ccc(Cl)c(CC2=NCCN2)c1] | 261.0 |
| 162 | 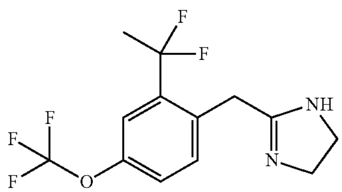 [SMILES: CC(F)(F)c1cc(OC(F)(F)F)ccc1CC1=NCCN1] | 309.0 |
| 163 | 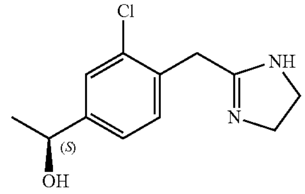 | 239.0 |
| 164 | 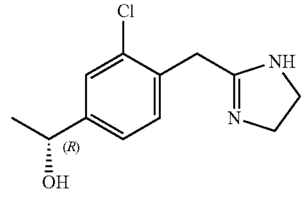 | 239.0 |
| 165 | 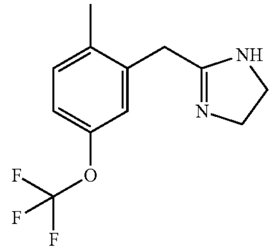 [SMILES: Cc1ccc(OC(F)(F)F)cc1CC1=NCCN1] | 259.0 |
| 166 | 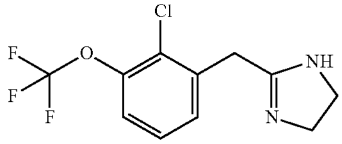 [SMILES: FC(F)(F)Oc1cccc(CC2=NCCN2)c1Cl] | 279.0 |

TABLE 1-continued

| Exemplary Compounds | | |
|---|---|---|
| Compound | Structure | [M + H] |
| 167 | 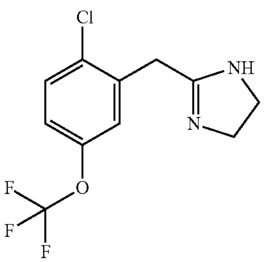 [SMILES: FC(F)(F)Oc1ccc(Cl)c(CC2=NCCN2)c1] | 279.0 |

In some embodiments, the present disclosure provides a compound from Table 1 or a pharmaceutically acceptable salt thereof.

EXAMPLES

Example I

Scheme 1 Preparation of Compound 22

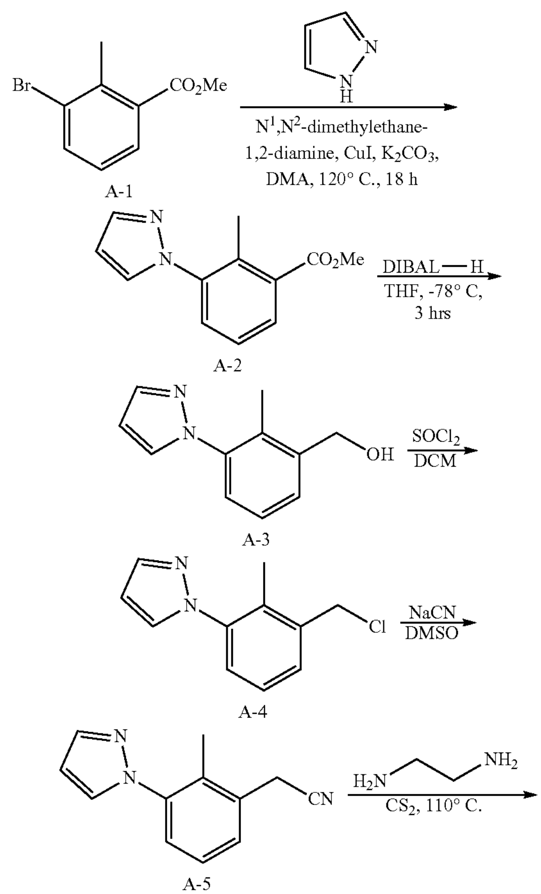

A-1, A-2, A-3, A-4, A-5

-continued

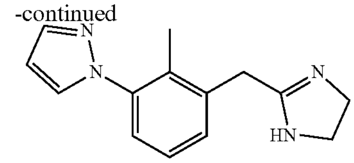

Compound 22

To a solution of ester A-1 (6 g, 26.19 mmol) in DMA (72 mL) was added pyrazole (8.92 g, 130.96 mol), $N^1,N^2$-dimethylethane-1,2-diamine (692.68 mg, 7.86 mmol), CuI (1.5 g, 7.86 mmol) and $K_2CO_3$ (10.86 g, 78.58 mol). The mixture was stirred at 120° C. for 12 h under $N_2$. TLC (petroleum ether/EtOAc 3:1, $R_f$=0.5) indicated about 70% of the starting material was remaining and 30% of desired product was detected. The reaction mixture was diluted with water (150 mL), extracted with EtOAc (3×80 mL). The combined organics were washed with brine (100 mL), dried over $Na_2SO_4$, filtered and concentrated under reduced pressure to give ester A-2 (0.6 g, 10% yield) as colorless oil; $^1H$ NMR (400 MHz, $CDCl_3$-d) δ 7.90-7.97 (m, 1H), 7.75 (d, J=1.4 Hz, 1H), 7.58 (d, J=2.3 Hz, 1H), 7.47-7.53 (m, 1H), 7.35 (t, J=7.8 Hz, 1H), 6.47 (t, J=2.0 Hz, 1H), 3.93 (s, 3H), 2.34 (s, 3H).

To a solution of ester A-2 (470 mg, 2.17 mmol) in toluene (5 ml) was added DIBAL-H (6.52 ml, 1 M) at −78° C. The mixture was stirred at −78° C. for 3 hrs. TLC (petroleum ether/EtOAc 2:1) indicated starting material was consumed and a new major spot was generated. The mixture was quenched with aqueous HCl (1 N, 30 ml) and extracted with EtOAc (3×10 ml). The organic layer was dried over $Na_2SO_4$, filtered and concentrated under reduced pressure to obtain alcohol A-3 (340 mg, 85% purity, 71% yield) as a white solid; $^1H$ NMR (400 MHz, $CDCl_3$-d) δ 7.79 (d, J=1.5 Hz, 1H), 7.61 (d, J=2.2 Hz, 1H), 7.55 (d, J=7.2 Hz, 1H), 7.25-7.34 (m, 2H), 6.51 (t, J=2.0 Hz, 1H), 4.63 (s, 2H), 3.08 (br s, 1H), 2.02 (s, 3H).

To a solution of alcohol A-3 (340 mg, 1.81 mmol) in DCM (5 mL) was added $SOCl_2$ (429.8 mg, 3.61 mmol) and catalytic amount of DMF. The mixture was stirred at 20° C. for 2 hrs. TLC (petroleum ether/EtOAc 2:1) showed N-4 was consumed, a new major spot generated. The mixture was neutralized with aqueous $NaHCO_3$ (20 mL) and the organic layer was separated and dried over $Na_2SO_4$, filtered and concentrated under reduced pressure to give benzyl chloride A-4 (340 mg, 90% purity, 82% yield) as a yellow solid; $^1H$ NMR (400 MHz, $CDCl_3$-d) δ 7.70 (d, J=1.3 Hz, 1H); 7.56 (d, J=2.3 Hz, 1H), 7.39 (dd, J=7.1, 1.59 Hz, 1H), 7.27 (br s, 2H), 6.43 (t, J=2.0 Hz, 1H), 4.64 (s, 2H), 2.20 (s, 2H), 2.14-2.25 (m, 1H).

To a solution of benzyl chloride A-4 (290 mg, 1.40 mmol) in DMSO (6 mL) was added NaCN (137.53 mg, 2.81 mmol). The mixture was stirred at 40° C. for 2 hrs. TLC showed all of starting material was consumed, a new major spot generated. The mixture was diluted with EtOAc (30 ml) and the combined organics were washed with water (3×10 ml), dried over $Na_2SO_4$, filtered and concentrated under reduced pressure. The residue was purified by prep-TLC (petroleum ether/EtOAc 2:1) to obtain nitrile A-5 (210 mg, 90% purity, 68% yield) as a yellow solid. $^1H$ NMR (400 MHz, $CDCl_3$-d) δ 7.74 (d, J=1.7 Hz, 1H); 7.59 (d, J=2.4 Hz, 1H), 7.48 (t, J=4.5 Hz, 1H), 7.30-7.38 (m, 2H), 6.47 (t, J=2.1 Hz, 1H), 3.76 (s, 2H), 2.15 (s, 3H); LCMS (ESI+): m/z 197.9 (M+1).

To a solution of nitrile A-5 (210 mg, 1.06 mmol) in ethane-1,2-diamine (2 mL) was added $CS_2$ (8.11 mg, 0.106 mmol). The mixture was stirred at 110° C. for 2 hrs. LCMS indicated that starting material was consumed, 97% of product with desired mass. The mixture was concentrated under reduced pressure. The residue was purified via prep-HPLC (Welch Xtimate C18 150*25 mm*5 um column, Mobile phase: A: $HCl/H_2O$=0.040% v/v;B: ACN) afforded compound 22 (42.8 mg, 99% purity, 17% yield) as a yellow solid; $^1$H NMR (400 MHz, $CD_3OD-d_4$) δ 7.91 (dd, J=18.4, 2.4 Hz, 1H), 7.50 (dd, J=7.2, 2.4 Hz, 1H), 7.49-7.30 (m, 1H), 6.64 (t, J=2.4 Hz), 4.07 (s, 2H), 3.96 (s, 4H), 2.06 (s, 3H); LCMS (ESI+): m/z 241.1 (M+1).

Example 2

Scheme 2 Preparation of Compound 27

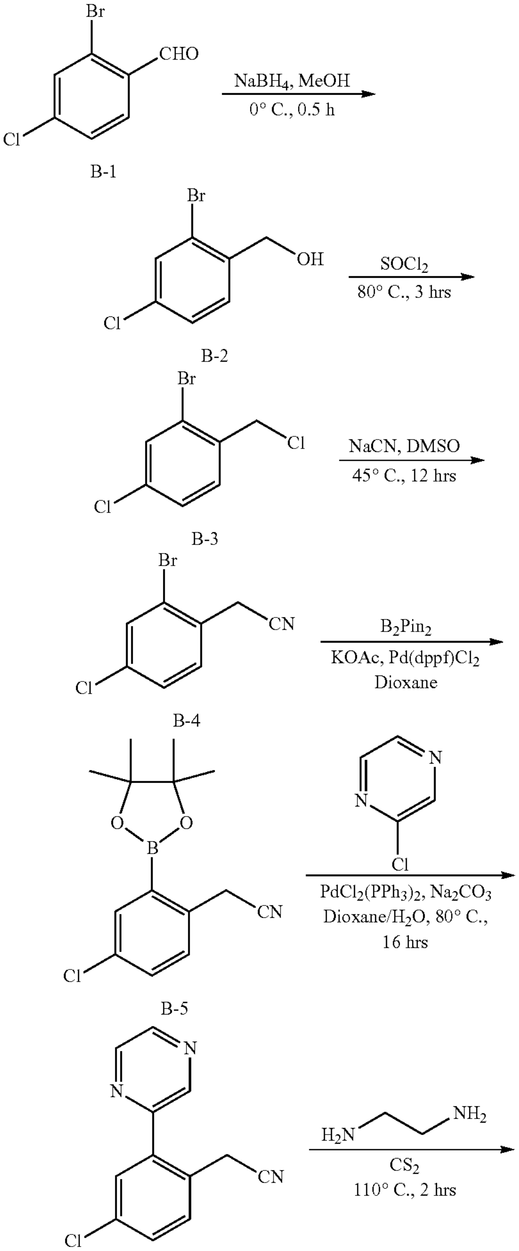

-continued

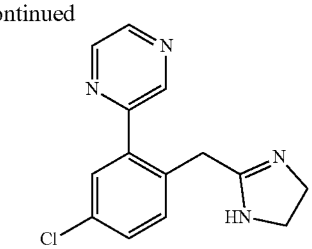

Compound 27

To a solution of 2-bromo-4-chlorobenzaldehyde (15 g, 68.35 mmol) in methanol (250 mL) was added sodium borohydride (2.72 g, 71.77 mmol) at 0° C. After 30 min TLC (3:1 petroleum ether/EtOAc) indicated the starting material was consumed and a new spot was detected. The mixture was quenched with water (120 mL) and concentrated and extracted extracted with ethyl acetate (2×150 mL). The organic layer was dried over $Na_2SO_4$, filtered and concentrated under reduced pressure to give alcohol B-2 (15 g, 100% yield) as white solid; H NMR (400 MHz, $CDCl_3$-d) δ 7.57 (d, J=1.9 Hz, 1H), 7.44 (d, J=8.2 Hz, 1H), 7.33 (dd, J=8.2, 1.91 Hz, 1H), 4.73 (s, 2H), 2.23-2.39 (m, 1H), 2.15 (br s, 1H).

A solution of alcohol B-2 (15 g, 67.73 mmol) in $SOCl_2$ (90 mL) was heated to 80° C. After 3 h TLC (3:1 petroleum ether/EtOAc) showed the starting material was consumed and a new spot was detected. The mixture was concentrated under reduced pressure to give a residue, which was purified via flash chromatography (silica gel, gradient 50/1 to 10/1 petroleum ether/EtOAc) to give benzyl chloride B-3 (10.3 g, 63% yield) as colorless oil; $^1$H NMR (400 MHz, $CDCl_3$-d) δ 7.63 (d, J=1.2 Hz, 1H), 7.44 (d, J=8.2 Hz, 1H), 7.33 (dd, J=8.3, 1.13 Hz, 1H), 4.68 (s, 2H).

To a solution of benzyl chloride, B-3 (22.3 g, 92.95 mmol) in 150 mL DMSO was added NaCN (7.29 g, 148.71 mmol). The mixture was heated to 45° C. After 3 h TLC (10:1 petroleum ether/EtOAc) showed all the starting material was consumed and a major spot generated. The mixture was cooled and diluted with 100 mL of water and extracted with EtOAc (2×100 mL). The organic layer was dried over $Na_2SO_4$, filtered and concentrated under reduced pressure to give a residue which was purified via flash chromatography (silica gel, eluted with petroleum ether/ethyl acetate=1/0 to 100/1) to give nitrile B-4 (18 g, 87% yield) as white solid; $^1$H NMR (400 MHz, $CDCl_3$-d) δ 7.63 (d, J=2.1 Hz, 1H), 7.44-7.50 (m, 1H), 7.37 (dd, J=8.3, 2.1 Hz, 1H), 3.82 (s, 2H).

To a solution of nitrile B-4 (6 g, 26.03 mmol) in anhydrous dioxane (200 mL) was added $B_2Pin_2$ (7.93 g, 31.24 mmol), KOAc (7.66 g, 78.09 mmol) and Pd(dppf)$Cl_2$ (180 mg) at 20° C. The reaction was degassed with $N_2$ for 2 mins then was heated at 90° C. for 12 hrs. TLC (5:1 petroleum ether/EtOAc) indicated that the starting material was consumed, and new spot was generated. The reaction mixture was diluted with water (500 mL) and extracted with EtOAc (3×200 mL). The combined organics were dried over $Na_2SO_4$, filtered and concentrated under reduced pressure to give a residue. Purification via flash column chromatography (silica, gradient 100/1 to 20/1 petroleum ether/EtOAc) to give a product pinacol boronate B-5 (4 g, 55% yield) was obtained as a white solid; $^1$H NMR (400 MHz, DMSO-$d_6$) δ=7.65 (d, J=2.4 Hz, 1H), 7.62-7.58 (m, 1H), 7.50-7.45 (m, 1H), 4.13 (s, 2H), 1.32 (s, 12H).

To a solution of pinacol boronate B-5 (300 mg 1.08 mmol) in 10 mL 4:1 Dioxane/$H_2O$ was added $Na_2CO_3$ (229.12 mg 2.16 mmol), 2-chloropyrazine (185.69 mg, 1.62 mmol) and $PdCl_2(PPh_3)_2$ (75.87 mg, 108.09 μmol). The mixture was stirred at 80° C. After 30 min LCMS indicated the starting material was consumed and 43% product with desired mass was detected. The reaction mixture was diluted with $H_2O$ (100 mL) and extracted with EtOAc (50 mL×3). The combined organics were washed with brine (50 mL×3), dried over $Na_2SO_4$ filtered and concentrated under reduced pressure to give a residue. The residue was purified via flash column chromatography (eluting with 100/1 to 20/1 petroleum ether/EtOAc) to give a product pyrazine B-6 (120 mg 48% yield) was obtained as a white solid; $^1H$ NMR (400 MHz, $CDCl_3$-d) δ 8.83 (d, J=1.1 Hz, 1H), 8.70-8.61 (m, 2H), 7.60-7.53 (m, 2H), 7.53-7.47 (m, 1H), 4.04 (s, 2H); LCMS (ESI+): m/z 230.1 (M+1).

To a solution of F-1 (100 mg 435.42 μmol) in ethane-1,2-diamine (3 mL) was added $CS_2$ (3.32 mg, 43.54 μmol). The mixture was stirred at 110° C. After 2 h LC-MS indicated the starting material was consumed and 49% product with desired mass was detected. The reaction mixture was concentrated under reduced pressure to give a residue. The residue was purified via Prep-HPLC (Column: Welch Xtimate C18 150*25 mm*5 um; Mobile phase: A: $HCl/H_2O$=0.040% v/v;B: ACN) to give Compound 27 (44.6 mg, 38% yield, HCl salt) as off-white solid.; $^1H$ NMR (400 MHz, $D_2O$) δ 8.79 (s, 1H), 8.76 (d, J=2.6 Hz, 1H), 8.69 (d, J=2.7 Hz, 1H), 7.67 (s, 1H), 7.64-7.58 (m, 1H), 7.50 (d, J=8.3 Hz, 1H), 3.97 (s, 2H), 3.73 (s, 4H); LCMS (ESI+): m/z 273.1 (M+1).

Example 3

Scheme 3 Preparation of Compound 40

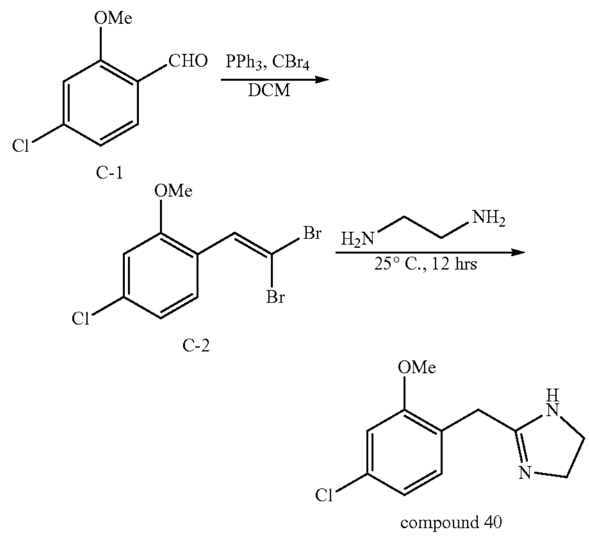

C-1

C-2 compound 40

To a solution of $PPh_3$ (1.23 g, 4.69 mmol) in dry DCM (20 mL) was added $CBr_4$ (777.59 mg 2.34 mmol) under nitrogen at 0° C. After 30 min a solution of 2-methoxy-4-chlorobenzaldehyde C-1 (200 mg, 1.17 mmol) in DCM (2 mL) was added to the mixture. After 2 h TLC (3:1 pet ether/EtOAc) indicated that all the starting material was consumed a new product was generated. The mixture was diluted with water (20 mL), extracted with DCM (3×20 mL). The combined organics were washed with brine (2×20 mL), dried over $Na_2SO_4$, filtered and concentrated under reduced pressure to give a residue. Purification via flash chromatography (silica gel, gradient 50:1 to 20:1 petroleum ether/EtOAc) to give bromide C-2 (0.25 g, yield 65%) as a yellow oil; $^1H$ NMR (400 MHz, $CDCl_3$-d) δ 7.63 (d, J=8.2 Hz, 1H), 7.52 (s, 1H), 6.96 (dd, J=8.2, 1.91 Hz, 1H), 6.86 (d, J=2.0 Hz, 1H), 3.84 (s, 3H).

A solution of dibromide C-2 (250 mg, 0.765 mmol) in ethyleneamine (2 mL) was stirred at 20° C. After 12 h LCMS indicated all of the starting material was consumed and 40% product with desired mass was generated. The mixture was concentrated to give a residue. The residue was purified by Pre-TLC (MeOH) and further purified by prep-HPLC (Mobile phase: A: $HCl/H_2O$=0.040% v/v; B: $CH_3CN$, Column: Welch Xtimate C18 150*25 mm*5 um) to give Compound 40 (16 mg, 10% yield) as white solid; $^1H$ NMR (400 MHz, $CD_3OD$-$d_4$) δ 7.29 (d, J=7.95 Hz, 1H), 7.11 (d, J=1.8 Hz, 1H), 7.03 (dd, J=8.1, 2.0 Hz, 1H), 3.92 (s, 4H), 3.91 (s, 3H), 3.84 (s, 2H); LCMS (ESI+): RT=1.627 min, m/z 225.0 (M+1).

Example 4

Scheme 4 Preparation of Compound 42

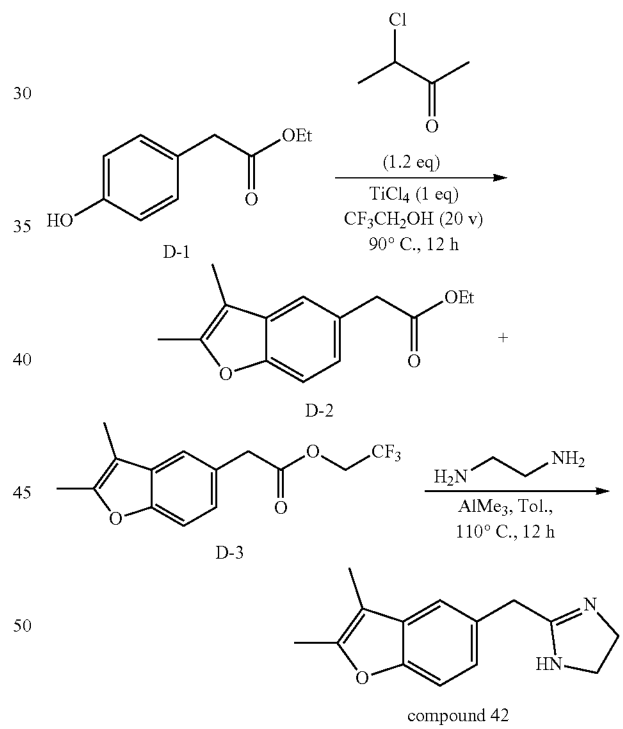

D-1

D-2

D-3 compound 42

A solution of phenol D-1 (2 g, 11.10 mmol, 1 eq) in $CF_3CH_2OH$ (10 mL) was heated at 110° C. for 30 min. $TiCl_4$ (2.11 g, 11.10 mmol) was added over 10 min. After 30 min a solution of 3-chlorobutan-2-one (1.42 g, 16.65 mmol, 1.2 eq) in $CF_3CH_2OH$ (10 mL) was added dropwise over 10 min. After 12 h TLC (pet ether/EtOAc 3:1) indicated most starting material was consumed and desired product was generated. The reaction mixture was poured into saturated $NH_4Cl$ (50 ml) and extracted with pet ether/EtOAc (30 ml×3). The combined organics were dried over $Na_2SO_4$, filtered and concentrated. The resulting residue was purified via flash chromatography to afford ester D-2 (0.2 g, 8% yield) as yellow oil; $^1H$ NMR (400 MHz, $CDCl_3$-d) δ 7.30-7.35 (m, 2H), 7.11 (dd, J=8.4, 2.0 Hz, 1H), 4.49 (q, J=8.8, 2H), 3.81 (s, 2H), 2.38 (s, 3H), 2.14 (s, 3H).

Ethane-1,2-diamine (77.62 mg, 1.29 mmol, 1.5 eq) was added to a solution of $AlMe_3$ (1.29 ml, 1.5 eq) in toluene (5 ml) at 0° C. After 30 min a solution of ester D-2 (0.2 g, 0.861 mmol, 1 eq) in toluene (3 mL) was added at 0° C. The mixture was stirred at 110° C. for 15 h to give a yellow mixture. TLC (3:1 pet ether/EtOAc) indicated the starting material was consumed and desired product was generated. The mixture was cooled to rt and quenched with MeOH (4 ml) and DCM (10 mL). The resulting mixture was filtered and concentrated. The residue was purified by prep-TLC (MeOH) and isolated via lyophization to give Compound 42 (27 mg, 14% yield) as a light-yellow solid. $^1H$ NMR (400 MHz, $CDCl_3$-d) δ 7.30-7.25 (m, 2H), 7.10 (d, J=6.3 Hz, 1H), 3.72 (s, 2H), 3.59 (s, 4H), 2.38 (s, 3H), 2.10 (s, 3H); LCMS (ESI+): RT=1.837 min, m/z 229.1 (M+1).

Example 5

Evaluation of Synthesized Adrenergic Receptor Agonists

Calcium flux experimental design: alpha-1 adrenergic receptors ($\alpha_1$-ARs) couple to $G_q$ proteins, which results in downstream activation of phospholipase C and release of calcium from intracellular stores. Intracellular calcium increase upon $\alpha_1$-AR activation can be detected by Calcium 6 dye.

Cell preparation: cells expressing an $\alpha_1$-AR were washed in warmed phosphate-buffered saline to remove medium and harvested using versene (Caisson Labs, catalog #EDL01). Cells were centrifuged at 250×g for 5 minutes, resuspended in growth medium, counted with a hemocytometer, seeded and incubated in a tissue culture incubator overnight in black, clear bottom 384 well plates (Corning cat. #3764), at 10,000 cells per well in between 30 and 50 μL growth media.

One vial of Calcium 6 dye (Molecular Devices cat. #R8190) was reconstituted according to manufacturer's instructions in 10 mL Hanks Balanced Salt Solution (HBSS, Corning cat. #45000-462) containing 20 mM HEPES (Caisson Labs cat. #HOL06) and stored at −20 deg C. On the day of assay, reconstituted Calcium 6 was diluted 1:8 in HBSS/HEPES containing 2 mM $CaCl_2$ (VWR cat. #E506) and 2 mM probenecid sodium salt (AAT Bioquest cat. #20061) to create cell dye solution. Media was removed from cells by tapping plates upside-down on absorbent wipes, followed by 15 second upside-down 50×g centrifugation, again on absorbent wipes. 12 μL cell dye solution was added to cells using a reagent dispenser (Integra viaFILL) and cells were incubated for 90 minutes at 37° C., 5% $CO_2$.

Compound preparation: candidate alpha-adrenergic compounds, dissolved to 10 mM in DMSO, were diluted in_assay buffer (HBSS/H-EPES containing 2 mM $CaCl_2$ and 2 mM probenecid sodium salt). Compound serial dilutions (10 concentrations, serially diluted in 5-fold increments) were prepared in assay buffer using 96 well plates (Corning 3365). On all assay plates, vehicle (DMSO) and positive control (10 μM epinephrine) conditions were included on the plate, as well as a dose-response curve of epinephrine. Completed 96 well compound plates were stamped into 384 well compound source plates (Corning 3657), 50 μL per well, using a viaFLO 384 or viaFLO 96 electronic pipette (Integra Biosciences) to create four technical replicate wells per dose. 384 well compound plates were centrifuged briefly at 250×g, sealed (Axygen PCR-SP) and incubated at 37° C. until the 90 minute cell dye incubation was complete.

Stimulation and Quantification of calcium flux: a Flexstation 3, controlled by Softmax Pro software v7.0.3 (Molecular Devices), pre-loaded with FLIPR Tetra Pipette Tips (Molecular Devices cat. #9000-0763), was set to 37° C. for at least 1 hour prior to the assay. Calcium 6 stained cells and 384 well compound plates were loaded onto the Flexstation and incubated on the machine for 5 minutes before initiating the assay.

Calcium 6 fluorescence was detected by exciting at 485 nm and measuring emission at 525 nm, with a 515 nm cutoff. For each assay well, baseline Calcium 6 fluorescence was detected for 18 seconds prior to 12 μL compound addition at 12 μL per second. Changes in Calcium 6 fluorescence were detected for a further 22 seconds, for a total read time of 40 seconds. All detection was performed with medium gain sensitivity, bottom read, with 6 flashes per read.

Data analysis: for calcium flux, analysis of maximum change from baseline over the 40-second read time was determined using Softmax Pro and data was exported as raw text files. Potency estimates ($EC_{50}$) were derived from dose response curves (maximum change from baseline versus the log concentration of test compound) fit by four-parameter nonlinear regression using Graphpad Prism. Efficacy was determined by comparing the magnitude of the test compound signal window (fitted curve max−min) with the signal window of the full agonist control, epinephrine. All dose-response curves on a given plate were simultaneously analyzed to define a single, shared baseline value, and the Hill slope was constrained to be >0, to avoid false curve fits from inactive compounds. All experiments were repeated a minimum of three times, with the average (mean) potency and maximum effect relative to the within-plate full agonist dose-response comparator reported.

The potency data is shown in Table 2 below.

TABLE 2

Assay Data for $\alpha_{1A}$-ARs

| Compound | Average PEC50 | Average Emax |
|---|---|---|
| 1 | C | C |
| 2 | C | C |
| 3 | C | C |
| 4 | C | C |
| 5 | B | B |
| 6 | B | B |
| 7 | B | B |
| 8 | C | C |
| 9 | B | B |
| 10 | B | B |
| 11 | C | C |
| 12 | B | C |
| 13 | B | A |
| 14 | B | B |
| 15 | C | C |
| 16 | B | B |
| 17 | C | C |
| 18 | B | A |
| 19 | C | A |
| 20 | B | B |
| 21 | B | A |
| 22 | B | B |
| 23 | B | B |
| 24 | B | B |
| 25 | A | A |
| 26 | B | C |
| 27 | B | B |
| 28 | A | A |
| 29 | B | B |
| 30 | A | A |
| 31 | C | C |

TABLE 2-continued

| Assay Data for $\alpha_{1A}$-ARs | | |
|---|---|---|
| Compound | Average PEC50 | Average Emax |
| 32 | B | A |
| 33 | C | C |
| 34 | C | B |
| 35 | A | A |
| 36 | C | C |
| 37 | B | B |
| 38 | B | B |
| 39 | B | A |
| 40 | B | B |
| 41 | C | C |
| 42 | C | C |
| 43 | B | B |
| 44 | B | B |
| 45 | B | A |
| 46 | B | B |
| 47 | B | B |
| 48 | B | A |
| 49 | A | A |
| 50 | B | B |
| 51 | C | B |
| 52 | B | C |
| 53 | A | A |
| 54 | B | B |
| 55 | B | B |
| 56 | B | B |
| 57 | B | B |
| 58 | B | B |
| 59 | B | A |
| 60 | B | B |
| 61 | B | C |
| 62 | C | C |
| 63 | B | B |
| 64 | C | C |
| 65 | B | A |
| 66 | B | B |
| 67 | B | A |
| 68 | C | C |
| 69 | B | B |
| 70 | B | B |
| 71 | B | B |
| 72 | C | C |
| 73 | B | B |
| 74 | B | A |
| 75 | B | A |
| 76 | B | B |
| 77 | B | A |
| 78 | A | A |
| 79 | A | A |
| 80 | C | B |
| 81 | B | A |
| 82 | B | B |
| 83 | C | B |
| 84 | B | B |
| 85 | B | B |
| 86 | B | B |
| 87 | B | B |
| 88 | B | A |
| 89 | C | B |
| 90 | C | B |
| 91 | B | A |
| 92 | C | B |
| 93 | B | A |
| 94 | B | B |
| 95 | B | B |
| 96 | C | B |
| 97 | C | C |
| 98 | B | B |
| 99 | C | B |
| 100 | A | A |
| 101 | A | A |
| 102 | B | B |
| 103 | C | B |
| 104 | B | A |
| 105 | B | B |
| 106 | B | B |
| 107 | A | B |
| 108 | B | A |
| 109 | B | A |
| 110 | B | A |
| 111 | B | A |
| 112 | B | A |
| 113 | B | A |
| 114 | B | B |
| 115 | C | B |
| 116 | B | A |
| 117 | B | B |
| 118 | C | C |
| 119 | C | C |
| 120 | C | C |
| 121 | B | B |
| 122 | B | A |
| 123 | B | A |
| 124 | B | B |
| 125 | B | A |
| 126 | B | B |
| 127 | B | A |
| 128 | B | B |
| 129 | B | B |
| 130 | B | A |
| 131 | B | B |
| 132 | B | A |
| 133 | B | B |
| 134 | B | A |
| 135 | B | B |
| 136 | B | B |
| 137 | B | B |
| 138 | B | A |
| 139 | C | B |
| 140 | C | A |
| 141 | C | A |
| 142 | B | B |
| 143 | B | A |
| 144 | C | B |
| 145 | C | C |
| 146 | C | C |
| 147 | B | B |
| 148 | B | A |
| 149 | C | B |
| 150 | C | B |
| 151 | B | B |
| 152 | C | C |
| 153 | B | C |
| 154 | C | B |
| 155 | B | B |
| 156 | B | B |
| 157 | B | A |
| 158 | B | B |
| 159 | C | B |
| 160 | B | A |
| 161 | B | A |
| 162 | C | B |
| 163 | B | A |
| 164 | A | A |
| 165 | B | A |
| 166 | B | B |
| 167 | B | A |

Ave $pEC_{50}$: A > 8.01; B = 8.00-6.01; C ≤ 6.00
Ave Emax: A > 61%; B = 21-60%; C ≤ 20%

Those skilled in the art will recognize, or be able to ascertain, using no more than routine experimentation, numerous equivalents to the specific composition and procedures described herein. Such equivalents are considered to be within the scope of this disclosure and are covered by the following claims.

What is claimed is:

1. A compound selected from:

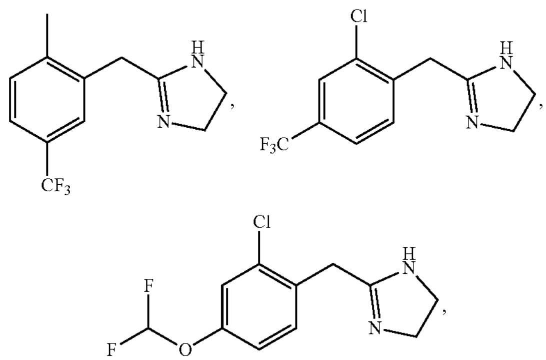

or a pharmaceutically acceptable salt thereof.

2. The compound of claim 1, wherein the compound is:

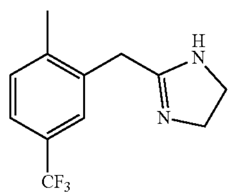

or a pharmaceutically acceptable salt thereof.

3. The compound of claim 1, wherein the compound is:

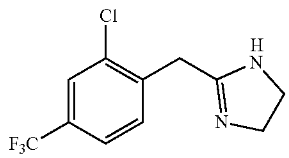

or a pharmaceutically acceptable salt thereof.

4. The compound of claim 1, wherein the compound is:

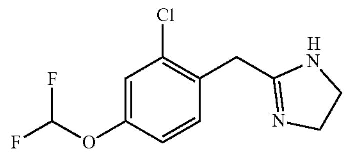

or a pharmaceutically acceptable salt thereof.

5. A pharmaceutical composition comprising the compound of claim 1 and a pharmaceutically acceptable excipient.

6. A pharmaceutical composition comprising the compound of claim 2 and a pharmaceutically acceptable excipient.

7. A pharmaceutical composition comprising the compound of claim 3 and a pharmaceutically acceptable excipient.

8. A pharmaceutical composition comprising the compound of claim 4 and a pharmaceutically acceptable excipient.

9. A method of treating a subject with a disease associated with an adrenergic receptor comprising administering to the subject a therapeutically effective amount of the compound according to claim 1, wherein the disease is one or more selected from the group consisting of MCI (mild cognitive impairment), aMCI (amnestic MCI), Vascular Dementia, Mixed Dementia, FTD (fronto-temporal dementia; Pick's disease), TBI (traumatic brain injury, CTE (chronic traumatic encephalopathy), stroke, DLB (dementia with Lewy bodies), PDD (Parkinson's disease dementia), ADHD (attention deficit hyperactivity disorder), Alzheimer's disease (AD), early AD, Down Syndrome (DS), and nOH.

10. The method of claim 9, wherein the disease is nOH.

11. The method of claim 9, wherein the subject is a human.

12. The method of claim 9, wherein the compound is administered to the subject through an oral, enteral, topical, inhalation, transmucosal, intravenous, intramuscular, intraperitoneal, subcutaneous, intranasal, epidural, intracerebral, intracerebroventricular, epicutaneous, extra-amniotic, intraarterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route.

* * * * *